US009790254B2

(12) United States Patent
Marco et al.

(10) Patent No.: US 9,790,254 B2
(45) Date of Patent: Oct. 17, 2017

(54) SELF-ASSEMBLED PEPTIDE NANOSTRUCTURES

(71) Applicant: Ramot at Tel-Aviv University Ltd., Tel-Aviv (IL)

(72) Inventors: Pini Marco, Bat-Yam (IL); Lihi Adler-Abramovich, Herzlia (IL); Ehud Gazit, Ramat-HaSharon (IL)

(73) Assignee: Ramot at Tel-Aviv University Ltd., Tel-Aviv (IL)

( * ) Notice: Subject to any disclaimer, the term of this patent is extended or adjusted under 35 U.S.C. 154(b) by 0 days.

(21) Appl. No.: 15/150,622

(22) Filed: May 10, 2016

(65) Prior Publication Data

US 2016/0326215 A1 Nov. 10, 2016

Related U.S. Application Data

(60) Provisional application No. 62/159,300, filed on May 10, 2015.

(51) Int. Cl.
| | | |
|---|---|---|
| *C07K 5/06* | (2006.01) | |
| *C07K 5/065* | (2006.01) | |
| *C09D 7/12* | (2006.01) | |
| *B82Y 40/00* | (2011.01) | |
| *B82Y 5/00* | (2011.01) | |

(52) U.S. Cl.
CPC .......... *C07K 5/06078* (2013.01); *B82Y 40/00* (2013.01); *C09D 7/1291* (2013.01); *B82Y 5/00* (2013.01)

(58) Field of Classification Search
None
See application file for complete search history.

(56) References Cited

FOREIGN PATENT DOCUMENTS

| | | |
|---|---|---|
| WO | WO 2004/052773 | 6/2004 |
| WO | WO 2004/060791 | 7/2004 |
| WO | WO 2007/043048 | 4/2007 |

OTHER PUBLICATIONS

Reches, Meital and Gazit, Ehud, "Casting metal nanowires within discrete self-assembled peptide nanotubes." Science (2003) p. 625-627.*
Adler-Abramovich, Lihi et al, "Patterned arrays of ordered peptide nanostructures." J. Nanosci. Nanotech. (2009) 9 p. 1701-1708.*
Bosne et al. "Piezoelectric Resonators Based on Self-Assembled Dipohenylalanine Mictrotubes", Applied Physics Letters, 102(7): 073504-1-073504-4, Feb. 18, 2013.
Carny et al. "Fabrication of Coaxial Metal Nanocables Using a Self-Assembled Peptide Nanotube Scaffold", Nano Letters, 6(8): 1594-1597, Published on Web Jul. 7, 2006.
Fleming et al. "Design of Nanostructures Based on Aromatic Peptide Amphiphiles", Chemical Society Reviews, 43(23): 8150-8177, Published Online Sep. 8, 2014.
Handelman et al. "Physics and Engineering of Peptide Supramolecular Nanostructures", Physical Chemistry Chemical Physics, PCCP, 14(8): 6391-6408, Published Online Mar. 29, 2012.
Hauser et al. "Peptides as Biological Semiconductors", Nature, 468(7323): 516-517, Nov. 25, 2010.
Jeon et al. "Self-Assembly of Cyclo-Diphenylalanine Peptides in Vacuum", The Journal of Physical Chemistry B, 118(24): 6644-6652, May 30, 2014.
Orbach et al. "The Rheological and Structural Properties of Fmoc-Peptide-Based Hydrogels: The Effect of Aromatic Molecular Architecture on Self-Assembly and Physical Characteristics", Langmuir, 28(4): 2015-2022, Jan. 5, 2012.
Ueda et al. "Rational Design of Peptide Nanotubes for Varying Diameters and Lengths", Journal of Peptide, 17(2): 94-99, Published Online Oct. 26, 2010.
Yemini et al. "Novel Electrochemical Biosensing Platform Using Self-Assembled Peptide Nanotubes", Nano Letters, 5(1): 183-186, Jan. 2005.
Adler-Abramovich et al. "Controlled Assembly of Peptide Nanotubes Triggered by Enzymatic Activation of Self-Immolative Dendrimers", ChemBioChem, 8(8): 859-862, May 25, 2007.
Adler-Abramovich et al. "Controlled Patterning of Peptide Nanotubes and Nanospheres Using Inkjet Printing Technology", Journal of Peptide Science, 14: 217-223, Published Online Nov. 26, 2007.
Adler-Abramovich et al. "Thermal and Chemical Stability of Diphenylalanine Peptide Nanotubes: Implications for Nanotechnological Applications", Langmuir, 22(3): 1313-1320, Published on Web Jan. 7, 2006.
Maity et al. "Co-Assembly of Aromatic Dipeptides Into Spherical Structures That Are Similar in Morphology to Red and White Blood Cells", Journal of Materials Chemistry B, 2(17): 2583-2591, 2014.
Reches et al. "Casting Metal Nanowires Within Discrete Self-Assembled Peptide Nanotubes", Science, XP002276672, 300(5619): 625-627, Apr. 25, 2003.
Reches et al. "Controlled Patterning of Aligned Self-Assembled Peptide Nanotubes", Nature Nanotechnology, XP002493888, 1(3): 195-200, Dec. 2006.
Reches et al. "Self-Assembly of Peptide Nanotubes and Amyloid-Like Structures by Charged-Termini-Capped Diphenylalanine Peptide Analogues", Israel Journal of Chemistry, XP009087914, 45(3): 363-371, Jun. 30, 2005.
Sedman et al. "Tuning the Mechanical Properties of Self-Assembled Mixed-Peptide Tubes", Journal of Microscopy, 249(3): 165-172, Epub Jan. 11, 2013.
Yuran et al. "Coassembly of Aromatic Dipeptides Into Biomolecular Necklaces", ACS Nano, 6(11): 9559-9566, Epub Oct. 19, 2012.
Adler-Abramovich et al. "Self-Assembled Arrays of Peptide Nanotubes by Vapour Deposition", Nature Nanotechnology, 4(12): 849-854, Published Online Oct. 18, 2009.

(Continued)

*Primary Examiner* — Fred Reynolds

(57) ABSTRACT

Nanostructures made up from two or more types of short peptides (e.g., aromatic dipeptides), which differ from one another by the presence (or absence) of an end-capping moiety, are disclosed. The disclosed nanostructures exhibit a closed tubular structure, short average length and narrow length distribution. Also disclosed are processes of preparing the nanostructures, articles comprising the nanostructures, and use of the nanostructures in, for example, reinforcement of materials.

17 Claims, 6 Drawing Sheets
(4 of 6 Drawing Sheet(s) Filed in Color)

(56) References Cited

OTHER PUBLICATIONS

Adler-Abramovich et al. "Self-Assembled Organic Nanostructures With Metallic-Like Stiffness", Angewandte Chemie, 122(51): 10135-10138, Published Online Sep. 28, 2010.
Amdursky et al. "Blue Luminescence Based on Quantum Confinement at Peptide Nanotubes", Nano Letters, XP055020819, 9(9): 3111-3115, Sep. 9, 2009.
Goerbitz "The Structure of Nanotubes Formed by Diphenylalanine, the Core Recognition Motif of Alzheimer's Beta-Amyloid Polypeptide", Chemical Communications, 22: 2332-2334, Published Online Apr. 13, 2006.
Kol et al. "Self-Assembled Peptide Nanotubes Are Uniquely Rigid Bioinspired Supramolecular Structures", Nano Letters, 5(7): 1343-1346, Published on Web Jun. 8, 2005.
Li et al. "Self-Assembly of Cationic Dipeptides Forming Rectangular Microtubes and Microrods With Optical Waveguiding Properties", Advanced Optical Materials, 3(2): 194-198, Feb. 1, 2015.
Loo et al. "Self-Assembled Proteins and Peptides as Scaffolds for Tissue Regeneration", Advanced Healthcare Materials, 4(16): 2557-2586, Nov. 1, 2015.
Mahler et al. "Rigid, Self-Assembled Hydrogel Composed of a Modified Aromatic Dipeptide", Advanced Materials, XP002446150, 18(11): 1365-1370, Apr. 25, 2006.
Orbach et al. "Self-Assembled Fmoc-Peptides as a Platform for the Formation of Nanostructures and Hydrogels", Biomacromolecules, 10(9): 2646-2651, Aug. 25, 2009.
Sedman et al. "Direct Observation of the Release of Phenylalanine From.Diphenylalanine Nanotubes", Journal of the American Chemical Society, JACS, 128(21): 6903-6908, May 31, 2006.
Yan et al. "Self-Assembly of Hexagonal Peptide Microtubes and Their Optical Waveguiding", Advanced Materials, 23(25): 2796-2801, Jul. 5, 2011.
Yemini et al. "Peptide Nanotube-Modified Electrodes for Enzyme-Biosensor Applications", Analytical Chemistry, 77(16): 5155-5159, Published on Web Jun. 30, 2005.

\* cited by examiner

FIG. 2C
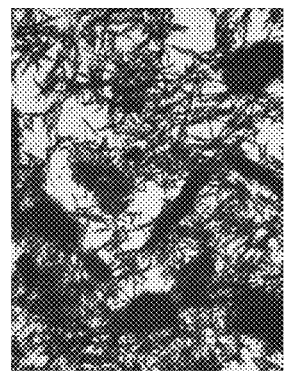
FIG. 2F
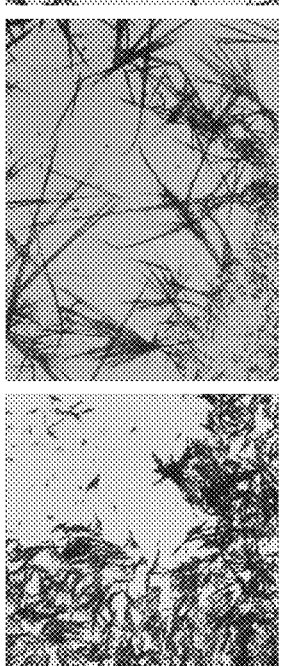
FIG. 2J
FIG. 2I
FIG. 2B
FIG. 2E
FIG. 2H
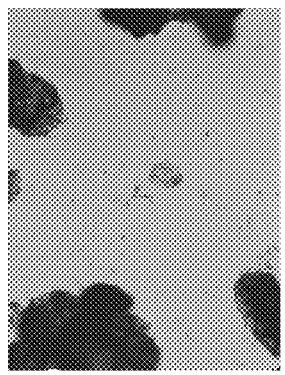
FIG. 2A
FIG. 2D
FIG. 2G

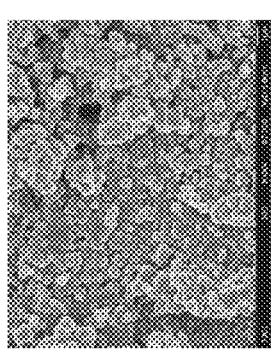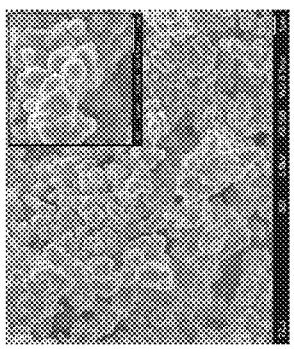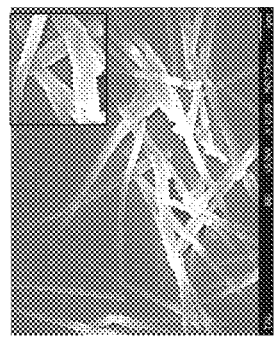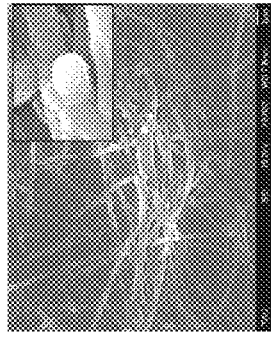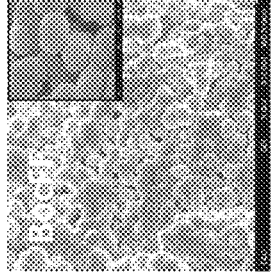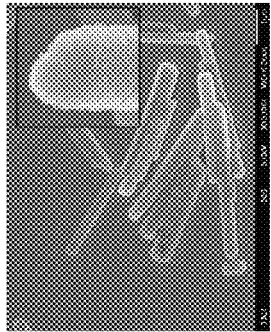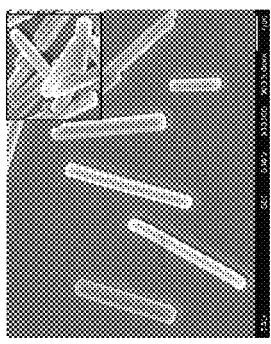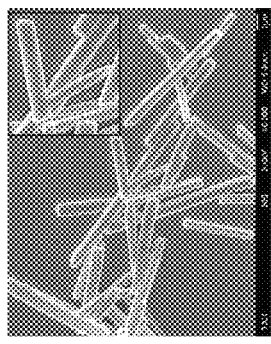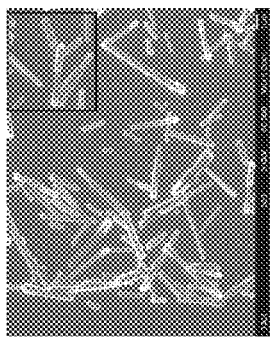

SELF-ASSEMBLED PEPTIDE NANOSTRUCTURES

RELATED APPLICATION

This application claims the benefit of priority under 35 USC 119(e) of U.S. Provisional Patent Application No. 62/159,300 filed May 10, 2015, the contents of which are incorporated herein by reference in their entirety.

FIELD AND BACKGROUND OF THE INVENTION

The present invention, in some embodiments thereof, relates to nanomaterials and, more particularly, but not exclusively, to self-assembled nanostructures composed of a plurality of dipeptides, to processes of generating same and to uses thereof.

Over the last few decades, molecular self-assembly has served as a cornerstone for the production of novel materials, which have already been incorporated into various applications in the fields of material science, electrical engineering and medicine. The ability to design basic building blocks which form self-assembly products with desired properties, in a bottom-up manner, has greatly promoted novel applications derived from such materials. In particular, the field of supramolecular polymers has gained much interest due to their ability to bridge the gap between covalent polymers and species formed by bottom-up self-assembly processes. The combination of supramolecular chemistry and polymer science has given rise to a rich diversity of supramolecular polymer nano- and micro-structures over the past two decades, including tubes, fibers, rods, films, plates, hydrogels, nanocages and vesicles.

The dynamic nature of the non-covalent interactions formed throughout the process of supramolecular polymers self-assembly enhance the ability to spatially and temporally control the formed end-product architectures. Furthermore, the unique molecular organization can be influenced by external stimuli, such as pH, temperature and the introduction of organic solvents. These stimuli may serve to alter the unique properties and characteristics of the formed non-covalent molecular polymers.

Similar to the well-studied covalent polymers, through the incorporation of two or more different building blocks, supramolecular co-polymers can be produced. As in the elongation of co-polymers, also in the case of supramolecular co-polymers, the incorporation of multiple building blocks significantly increases the chemical diversity and conformational space of available polymers. Peptide building blocks feature biocompatibility, chemical flexibility and versatility, biological recognition abilities and facile synthesis, and therefore serve as attractive organic building block for bionanotechnology applications.

Short aromatic peptides, particularly aromatic dipeptides such as the diphenylalanine aromatic core of the β-amyloid polypeptide, have been shown to undergo self-assembly to form well-ordered hollow tubular nanostructures in aqueous solution [Reches M, Gazit E. *Science* 2003; 300: 625-627]. These self-assembled aromatic dipeptide nanostructures have remarkable chemical and thermal stability and extraordinary mechanical strength [Sedman et al. *J. Am. Chem. Soc.* 2006; 128: 6903-6908; Adler-Abramovich et al. *Langmuir* 2006; 22: 1313-1320].

The self-assembly of aromatic dipeptide nanostructures has been performed by horizontal and vertical alignment of nanostructures and a controlled self-assembly has also been obtained using enzymatic activation of self-immolative dendrimers [Reches and Gazit E. *Nat. Nanotechnol.* 2006; 1:195-200; Adler-Abramovich et al. *ChemBioChem* 2007; 8: 859-862].

Aromatic dipeptide nanostructures where shown to serve as a degradable mold for the fabrication of silver nanowires, as a scaffold for the organization of platinum nanoparticles and as a template for the formation of coaxial nanocables [Carny et al. *Nano Lett.* 2006; 6: 1594-1597; Song et al. *Chem. Commun.* 2004; 9:1044-1045].

Peptide tubular nanostructures were also used for the fabrication of sensitive electrochemical biosensors, and for the formation of biocompatible hydrogels [Yemini et al. *Anal. Chem.* 2005; 77: 5155-5159; Yemini et al. *Nano Lett.* 2005; 5: 183-186; Mahler et al. *Adv. Mater.* 2006; 18: 1365-1370].

WO 2004/052773 and WO 2004/060791 disclose self-assembled peptide tubular nanostructures made of short aromatic peptides, and their use as, for example, a casting mold for metal nanowires, for the fabrication of peptide-nanotube platinum-nanoparticle composites, and in electrochemical biosensing platforms.

WO 2007/0403048 and Reches and Gazit [*Isr. J. Chem.* 2005; 45: 363-371] discloses the assembly of tubular and fibrillar (amyloid-like) structures by non-charged, end-capping modified aromatic peptides and, particularly, by diphenylalanine analogs such as, for example, Boc-Phe-Phe-OH and Fmoc-Phe-Phe-OH peptides.

Adler-Abramovich et al. [*J. Pept. Sci.* 2008; 14: 217-223] describe that two types of nanostructures; nanotubes and nanospheres; are obtained by the self-assembly of the aromatic dipeptide Phe-Phe, while using different end-capping moieties. Spherical nanotubes are self-assembled while using tertbutoxycarbonyl-Phe-Phe-OH (Boc-Phe-Phe-OH), and fibrillar nanostructures are self-assembled while using Fmoc-Phe-Phe-OH. It has been shown that both spherical and tubular structures could be efficiently used as an 'ink' and patterned on transparency foil and ITO plastic surfaces using a commercial inkjet printer.

It has recently been shown that the co-assembly of short peptide building blocks can produce complex architectures such as "beads on a string", hydrogels and tubes. This co-assembly into supramolecular co-polymers allows modulation of the architecture and the physical and mechanical properties of such ultra-structures. See, for example, Orbach et al. *Langmuir* 2012, 28, 2015-2022; Carny et al. *Nano Lett.* 2006, 6, 1594-7.

Sedman et al. [J. of Microscopy, 2013, pp. 1-8] teach nano- and micro-scale fibrillar and tubular structures formed by mixing two aromatic dipeptides, Phe-Phe and D-Nal-Nal, and describe that the mechanical properties of the structures depend on the percentage of each peptide in the mixture.

Yuran et al. [*ACS Nano*, 2012, 6 (11), pp 9559-9566] describes the formation of complex peptide-based structures by the co-assembly of Phe-Phe-OH and Boc-Phe-Phe-OH, into a construction of beaded strings, where spherical assemblies are connected by elongated elements.

Maity et al. [*J. Mater. Chem. B*, 2014, 2, 2583-2591] describes the co-assembly of two aromatic dipeptides, diphenylalanine and Fmoc-L-DOPA(acetonated)-D-Phe-OMe, into different spherical structures that are similar in morphology to either red or white blood cells.

SUMMARY OF THE INVENTION

The present inventors have now devised and successfully prepared and practiced a composite material formed by self-assembly of two types of aromatic dipeptides, which differ from one another by the type and/or presence of their end-capping moiety.

The present inventors have uncovered, for example, that addition of Boc-Phe-Phe-OH (Boc-FF), dissolved in EtOH, to an excess of charged (non-end-capped Phe-Phe (FF) dipeptide, dissolved in hot water (e.g., 80° C.), resulted in self-assembled structures during the cool down process. These structures exhibit an average length and morphology which are different from structures made of each dipeptide alone, and are therefore referred to herein also as "hydrid nanostructures" or "composite nanostructures".

The obtained hybrid structures exhibit morphology of elongated tubular nanostructure, optionally closed tubular nanostructures in which the tubes' cap is closed. The hybrid nanostructures are characterized by a diameter within the range of, for example, 90 nm to 230 nm, and are relatively short, having a average length that ranges, for example, from 1 to 10 μm, or from 1 to 6 μm and even lower. The "closed" structure and relatively short length of these hybrid structures attribute to the structure beneficial mechanical strength properties and further make these structures suitable for reinforcement of composite materials.

According to an aspect of some embodiments of the present invention there is provided a composition comprising a plurality of tubular nanostructures, wherein at least 80% of the nanostructures are characterized by a length smaller than 10 microns, each of the nanostructures being formed of a plurality of aromatic dipeptides, the plurality of aromatic dipeptides comprising at least two different types of aromatic dipeptides, at least one type of the aromatic dipeptides being an end-capping modified aromatic dipeptide and at least one type of aromatic dipeptides being a non-modified aromatic dipeptide, wherein a molar ratio of the at least two types of aromatic dipeptides in the plurality of aromatic dipeptides is such that provides tubular nanostructures characterized by the length.

According to some of any of the embodiments described herein, at least 50% of the nanostructures are characterized as closed tubular structures.

According to some of any of the embodiments described herein, at least 80% of the nanostructures are characterized by a length smaller than 8 microns.

According to some of any of the embodiments described herein, the molar ratio of the end-capping modified aromatic homodipeptide and the non-modified aromatic homodipeptide ranges from 1:5 to 1:100.

According to some of any of the embodiments described herein, the molar ratio ranges from 1:5 to 1:50.

According to an aspect of some embodiments of the present invention there is provided a composition comprising a plurality of tubular nanostructures, each of the nanostructures being formed of a plurality of aromatic dipeptides, the plurality of aromatic dipeptides comprising at least two different types of aromatic dipeptides co-assembled with one another, at least one type of the aromatic dipeptides being an end-capping modified aromatic dipeptide and at least one type of aromatic dipeptides being a non-modified aromatic dipeptide, wherein a length distribution of the nanostructures has a full-width-at-half-maximum (FWHM) of less than 10 microns.

According to an aspect of some embodiments of the present invention there is provided a composition comprising a plurality of tubular nanostructures, each of the nanostructures being formed of a plurality of aromatic dipeptides, the plurality of aromatic dipeptides comprising at least two different types of aromatic dipeptides co-assembled with one another, at least one type of the aromatic dipeptides being an end-capping modified aromatic dipeptide and at least one type of aromatic dipeptides being a non-modified aromatic dipeptide, wherein a length distribution of the nanostructures has a full-width-at-half-maximum (FWHM) which lower by at least 5, or at least 10 microns of a full-width-at-half-maximum (FWHM) of a length distribution of nanostructures formed of the non-modified aromatic dipeptide.

According to some of any of the embodiments described herein, at least 50% of the nanostructures are characterized as closed tubular structures.

According to some of any of the embodiments described herein, at least 80% of the nanostructures are characterized by a length smaller than 10 microns.

According to some of any of the embodiments described herein, a molar ratio of the at least two types of aromatic dipeptides in the plurality of aromatic dipeptides is such that provides tubular nanostructures characterized by the length distribution.

According to some of any of the embodiments described herein, the molar ratio of the end-capping modified aromatic homodipeptide and the non-modified aromatic homodipeptide ranges from 1:5 to 1:100.

According to some of any of the embodiments described herein, the molar ratio ranges from 1:5 to 1:50.

According to some of any of the embodiments described herein, each of the end-capping modified dipeptides comprises a non-aromatic end capping moiety. According to some of any of the embodiments described herein, each of the end-capping modified dipeptides is an N-terminus modified peptide.

According to some of any of the embodiments described herein, the non-aromatic end capping moiety is tert-butoxycarbonyl (Boc).

According to some of any of the embodiments described herein, each of the end-capping modified dipeptides is a homodipeptide.

According to some of any of the embodiments described herein, each of the non-modified aromatic dipeptides is a homodipeptide.

According to some of any of the embodiments described herein, each of the homodipeptides is a phenylalanine-phenylalanine dipeptide.

According to some of any of the embodiments described herein, each of the end-capping modified dipeptides each of the end-capping modified dipeptides is an N-terminus modified peptide, and wherein the end capping moiety is tert-butoxycarbonyl (Boc).

According to an aspect of some embodiments of the present invention there is provided a process of generating a composition comprising a plurality of tubular nanostructures formed of at least two different types of aromatic dipeptides co-assembled with one another, at least one type of the aromatic dipeptides being an end-capping modified aromatic dipeptide and at least one type of aromatic dipeptides being a non-modified aromatic dipeptide, in solution, the process comprising contacting a first solution comprising a plurality of the end-capping modified aromatic dipeptides and a first solvent and at least a second solution comprising a plurality of the non-modified aromatic dipeptides and a second solvent, to thereby obtain a mixture of the first and second solutions, thereby generating the composition.

According to some of any of the embodiments described herein, the contacting is effected at elevated temperature.

According to some of any of the embodiments described herein, the process further comprises, subsequent to the contacting, cooling down the mixture of the first and second solutions.

According to an aspect of some embodiments of the present invention there is provided a process of controlling an average length and/or a length distribution of tubular nanostructures formed of a plurality of aromatic dipeptides in solution, the process comprising contacting a first solution comprising a plurality of end-capping modified aromatic dipeptides and a first solvent and at least a second solution comprising a plurality of the non-modified aromatic dipeptides and a second solvent, to thereby obtain a mixture of the first and second solutions, wherein the average length and/or the length distribution is/are determined by a molar ratio of the end-capping modified aromatic dipeptide and the non-modified aromatic dipeptide.

According to an aspect of some embodiments of the present invention there is provided an article-of-manufacturing comprising the composition as described herein in any of the respective embodiments.

According to some of any of the embodiments described herein, the article-of-manufacturing comprises the plurality of nanostructures dispersed in a matrix or deposited on a surface of a substrate within the article.

According to some of any of the embodiments described herein, the article of manufacturing comprises a material reinforced by the composition.

According to an aspect of some embodiments of the present invention there is provided a method of reinforcing a material, the method comprising introducing to the material the composition as described herein in any of the respective embodiments.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 1 is a graph showing the yield of a nanostructure formed from various combinations of the aromatic dipeptides FF and Boc-FF;

Figure 4A:
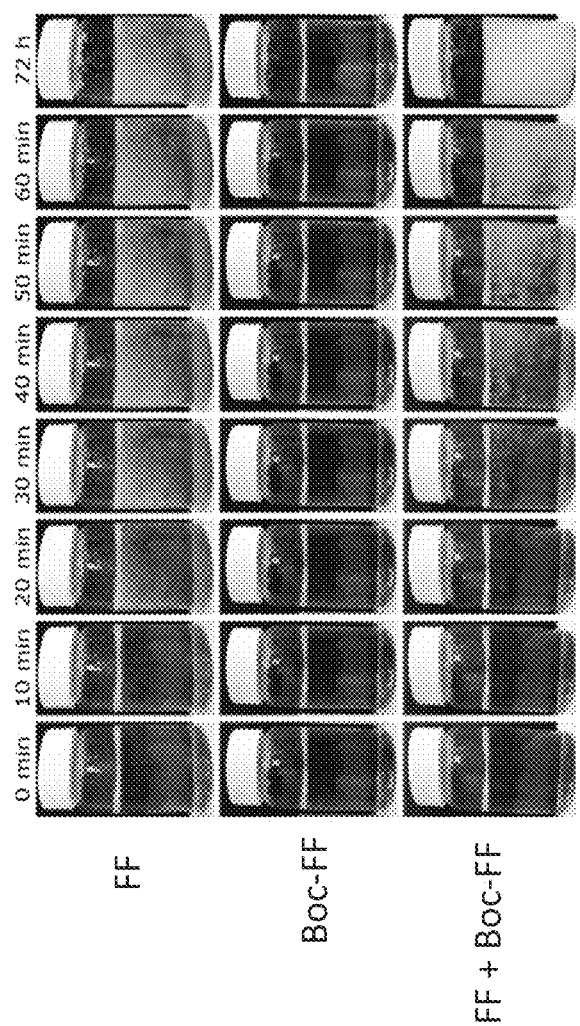
Figure 4B:
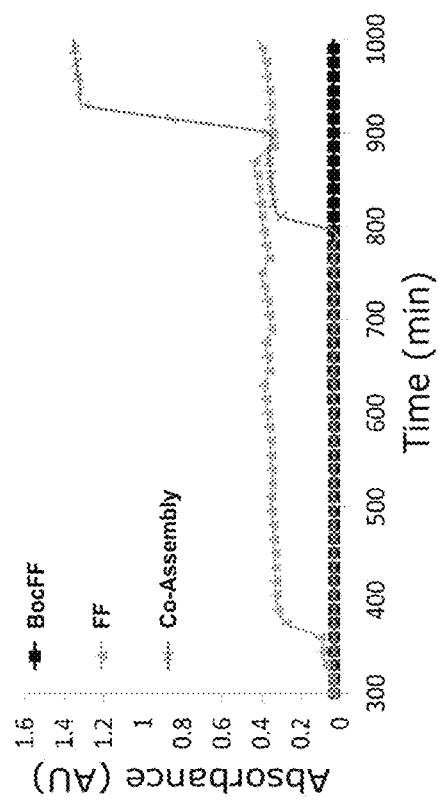
Figure 6:
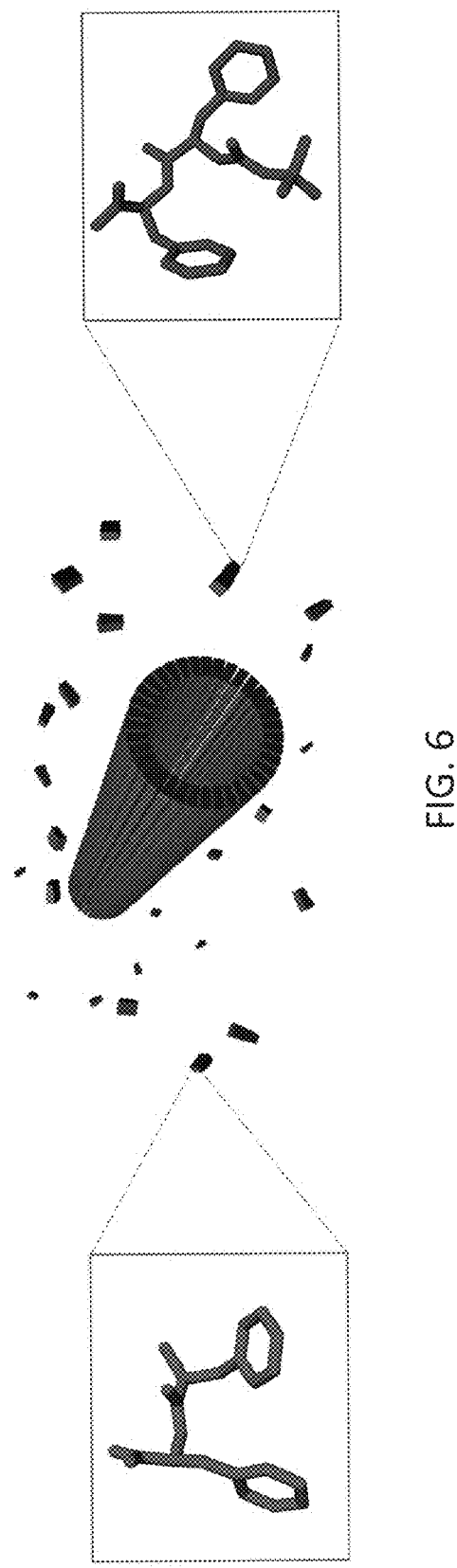

FIGS. 2A-J present light microscopy images of nanostructures formed from various combinations of FF and Boc-FF;

FIGS. 3A-J present SEM images of nanostructures formed from various combinations of the aromatic dipeptides FF and Boc-FF;

FIGS. 4A-B present image sequences of the assembly process in water of 2 mg/ml FF (upper panel), 0.125 mg/ml Boc-FF (middle panel) and co-assembly of FF:Boc-FF at 20:1 molar ratio; 2 mg/ml FF+0.125 mg/ml Boc-FF (lower panel) (FIG. 4A), with the solution volume in each vial being 15 ml; and a plot showing absorbance at 400 nm over time for each solution (FIG. 4B);

FIGS. 5A-D are bar graphs presenting the length distribution of nanostructures forms from FF alone (FIG. 5A), 20:1 (molar ratio) FF and Boc-FF (FIG. 5B); 5:1 (molar ratio) FF and Boc-FF (FIG. 5C); and 10:1 (molar ratio) FF and Boc-FF (FIG. 5D), while Insets show transmission electron microscopy images of the peptide assemblies at the different FF:Boc-FF ratios, Scale bar=10 µm;

FIG. 6 presents a schematic presentation of the co-assembly of FF:Boc-FF naotubes.

DESCRIPTION OF SPECIFIC EMBODIMENTS OF THE INVENTION

The present invention, in some embodiments thereof, relates to nanomaterials and, more particularly, but not exclusively, to self-assembled nanostructures composed of a plurality of dipeptides, to processes of generating same and to uses thereof.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Molecular self-assembly of peptides into ordered nanotubes is highly important for various technological applications. Very short peptide building blocks, as short as dipeptides, can form assemblies with unique mechanical, optical, piezoelectric and semiconductive properties.

One of the most well studied archetypical building blocks, which forms supramolecular polymers through self-assembly, is the diphenylalanine peptide (FF). This recognition and self-assembly module is a minimal peptide sequence, which has been shown to self-assemble to form polymer-like nano-assemblies [Reches and Gazit 2003, supra; Görbitz, C. H. *Chem. Commun.* 2006, 22, 2332-2334].

The formed tubular structures have been extensively studied over the past decade, and their unique properties were characterized [see, for example, Li et al. *Adv. Opt. Mater.* 2015, 3, 194-198; Yan et al. *Adv. Mater.* 2011, 23, 2796-2801; Amdursky et al. *Nano Lett.* 2009, 9, 3111-3115; Hauser and Zhang, *Nature* 2010, 468, 516-517; Bosne et al. *Appl. Phys. Lett.* 2013, 102, 073504; Handelman et al. *Phys. Chem. Chem. Phys.* 2012, 14, 6391-6408].

Since these nanotubes self-assemble in solution in an inherently sequential process, it may result in formation of a wide range of nanotubes sizes. The length of the tubular structures, deposited on a solid surface, can be controlled while using physical vapor deposition method that does not involve solution phase [Adler-Abramovich et al. *Nat. Nanotechnol.* 2009, 4, 849-854].

In addition, it was shown that right-handed and left-handed amphiphilic helical peptides, containing 35-38 amino acids, were mixed to form peptide nanotubes with varying dimensions based on the helix-chirality of the peptides [Ueda et al. *J. Pept. Sci.* 2011, 17, 94-99].

However, the challenge of controlling dipeptide nanotubes dimension in solution still remains.

Derivatives and analogues of the FF peptide had also been extensively examined and also show unique characteristics. Modifications of the charged termini paved the way to the formation of various peptide analogues based on electrostatic considerations. It was reported that the N-(tert-butoxycarbonyl)-L-Phe-L-Phe-COOH (Boc-FF) can alternately self-assemble into tubular or spherical structures under different solvent environment conditions [Reches ad Gazit, 2005, supra; Adler-Abramovich and Gazit. *J. Pept. Sci.* 2008, 14, 217-223]. Boc-FF can undergo self-assembly into structurally distinct states on the nanometer scale as a result of variations in the solvent composition in which the process occurs.

In Boc-FF, the uncharged Boc group is attached to the N-terminus of the dipeptide, leaving the aromatic residues free to interact. It has been shown that alternating the N-terminus charge via the addition of a Boc or another group at the peptide terminus still allows for FF-like structure formation [Reches ad Gazit, 2005, supra]. Molecular dynamics simulations suggest that the N-terminus contributes to the stabilization of early-stage aggregates, while the final tube structure does not rely on the charged termini regions [Jeon and Shell, J. Phys. Chem. B 2014, 118, 6644-6652].

In a search for methodologies for generating self-assembled peptide nanotubes (PNT) with controlled length, in solution, the present inventors have uncovered that by applying a co-assembly approach, the elongation and length-distribution of tubular structures can be regulated, by adjusting the molecular ratio of the peptides in solution.

The present inventors have demonstrated that this approach enables control over the self-assembly process, which is continuous by nature. The integration of two types of peptide building blocks in the same nanometric architecture results in formation of more complex structures and expends their physical properties, leading to diverse new properties that can be integrated into various technological applications.

The present inventors have demonstrated that the integration of Boc-FF building blocks during the assembly of FF peptide nanotubes can alter the formed structures dimensions. Without being bound by any particular theory, it is assumed that while the two building blocks share an overlapping peptide sequence which may facilitate the aromatic moieties interactions, the N-terminus modification of the Boc-FF peptide interferes with the assemblies' elongation.

The present inventors have explored the morphology, PNT formation kinetics, and length distribution of nanostructures formed of various ratios of diphenylalanine (Phe-Phe; FF) and its N-capped analogue Boc-FF.

Figure 1:
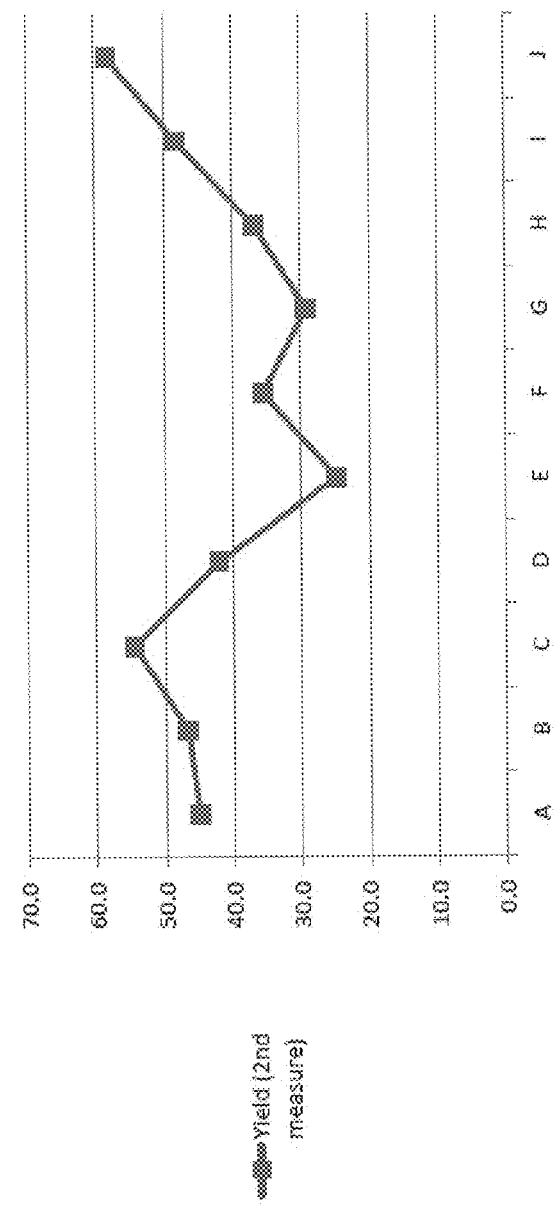

FIG. 1 presents the yield of nanostructures formed at various molar ratios of the peptide building blocks. FIGS. 2A-J and 3A-J present SEM and TEM micrographs, respectively, demonstrating the high aspect ratio of the tubular structure formed of FF, whereby addition of the Boc-FF to the FF solution resulted in the shortening of the ordered structures. The electron microscopy images further show that the co-assembled structures generally feature termini with a capped architecture, which is distinct from the hollow nature of the FF tubes.

Kinetic analysis, shown in FIGS. 4A-B, suggested a slower co-assembly organization process as compared to the self-assembly dynamics of each of the peptide building blocks separately, which is consistent with a hierarchal arrangement of the peptide moieties within the co-assemblies. The peptide nanotubes length distribution, as determined by electron microscopy, shown in FIGS. 5A-D, indicated narrower length distribution of the hybrid structures, compared to the FF nanostructures.

FIG. 6 schematically illustrates the random integration of the Boc-FF peptide along the FF tubes during co-assembly, as deduced from the accumulated data.

These studies have revealed a simple and efficient mechanism for the control of nanotube sizes through the co-assembly of peptide entities at various ratios, allowing for the desired end-product formation. This dynamic size control offers a new level of molecular engineering at the nano-scale exploiting the advantages of molecular co-assembly.

Embodiments of the present invention therefore relate to novel tubular nanostructures, made of two or more typed of aromatic dipeptides, co-assembled with one another, which are also referred to herein as "hybrid nanostructures" or "hybrid tubular nanostructures" or simply as "nanostructures".

Embodiments of the present invention further relate to processes of generating these nanostructures in solution, and to processes of regulating the length and length distribution of these nanostructure.

Embodiments of the present invention further relate to compositions and articles-of-manufacturing comprising these nanostructures and to uses thereof. The shorter average and narrower length distribution render these nanostructures highly suitable in applications where homogenous dispersion of the nanostructures in a matrix is desirable.

The Hybrid Nanostructures:

According to an aspect of some embodiments of the present invention there is provided a nanostructure formed of a plurality of aromatic dipeptides. The plurality of aromatic dipeptides comprises at least two types of aromatic dipeptides. The two or more types of aromatic dipeptides are co-assembled with one another in the nanostructure.

In some embodiments, the nanostructure is a tubular nanostructure.

As used herein the phrase "tubular nanostructure" refers to a spherical or elongated tubular or conical structure having a diameter or a cross-section of less than 1 μm (preferably less than 500 nm, and more preferably less than about 300 nm).

Further preferably, the tubular nanostructure described herein is hollowed.

In some embodiments, the phrase "tubular nanostructure" refers to an elongated tubular structure.

In some embodiments, the tubular nanostructure is a self-assembled tubular nanostructure, and in some embodiments, the tubular structure is self-assembled in a solution comprising the peptides forming the nanostructure. The solution is preferably an aqueous solution.

In some embodiments, the tubular nanostructure is characterized by a diameter that ranges from 50 nm to 300 nm, including any subranges and intermediate value therebetween.

In some of any of the embodiments described herein, the nanostructure is formed of two or more types of peptides, as described herein, co-assembled with one another.

The peptides forming the nanostructure are also referred to herein as "building blocks".

By "co-assembled" it is meant that peptides of one type are interlaced with peptides of another type in the same nanostructure. In other words, the term "co-assembled" means that at least a portion of the peptides of a first type are in interaction with at least a portion of the peptides of another type within the nanostructure. That is, the two or more types of peptides serve together as building blocks of the nanostructures.

The nanostructures of the present embodiments are also referred to herein as "hybrid nanostructures".

The term "peptide" as used herein encompasses native peptides (either degradation products, synthetically synthesized peptides or recombinant peptides) and peptidomimetics (typically, synthetically synthesized peptides), as well as peptoids and semipeptoids which are peptide analogs. Such modifications include, but are not limited to N terminus modification, C terminus modification, peptide bond modification, including, but not limited to, $CH_2$—NH, $CH_2$—S, $CH_2$—S=O, O=C—NH, $CH_2$—O, $CH_2$—$CH_2$, S=C—NH, CH=CH or CF=CH, backbone modifications, and residue modification. Methods for preparing peptidomimetic compounds are well known in the art and are specified, for example, in Quantitative Drug Design, C. A. Ramsden Gd., Chapter 17.2, F. Choplin Pergamon Press (1992), which is incorporated by reference as if fully set forth herein. Further details in this respect are provided hereinunder.

Peptide bonds (—CO—NH—) within the peptide may be substituted, for example, by N-methylated bonds (—N($CH_3$)—CO—), ester bonds (—C(R)H—C—O—O—C(R)—N—), ketomethylen bonds (—CO—$CH_2$—), α-aza bonds (—NH—N(R)—CO—), wherein R is any alkyl, e.g., methyl, carba bonds (—$CH_2$—NH—), hydroxyethylene bonds (—CH(OH)—$CH_2$—), thioamide bonds (—CS—NH—), olefinic double bonds (—CH=CH—), retro amide bonds (—NH—CO—), peptide derivatives (—N(R)—$CH_2$—CO—), wherein R is the "normal" side chain, naturally presented on the carbon atom. These modifications can occur at any of the bonds along the peptide chain and even at several (2-3) at the same time.

As used herein throughout, the term "amino acid" or "amino acids" is understood to include the 20 naturally occurring amino acids; those amino acids often modified post-translationally in vivo, including, for example, hydroxyproline, phosphoserine and phosphothreonine; and other unusual amino acids including, but not limited to, 2-aminoadipic acid, hydroxylysine, isodesmosine, nor-valine, nor-leucine and ornithine. Furthermore, the term "amino acid" includes both D- and L-amino acids.

Natural aromatic amino acids, Trp, Tyr and Phe, may be substituted for synthetic unnatural acid such as phenylglycine, TIC, naphthylalanine (Nal), ring-methylated derivatives of Phe, halogenated derivatives of Phe or O-methyl-Tyr, and β amino-acids.

In addition to the above, the peptides of the present invention may also include one or more modified amino acids (e.g., biotinylated amino acids) or one or more non-amino acid monomers (e.g. fatty acids, complex carbohydrates etc).

According to the present embodiments, each peptide in the plurality of peptides comprises two amino acid residues and therefore the nanostructure is formed from a plurality of dipeptides.

According to the present embodiments, each peptide in the plurality of peptides comprises at least one aromatic amino acid residue, and is referred to herein as an aromatic peptide.

According to the present embodiments, at least a portion of, or each peptide in, the plurality of peptides comprises two amino acid residues, at least one of the amino acid residues being an aromatic amino acid residue, and is referred to herein as an aromatic dipeptide.

The phrase "aromatic amino acid residue", as used herein, refers to an amino acid residue having an aromatic moiety for a side-chain, such as, for example, a substituted or unsubstituted naphthalenyl and/or a substituted or unsubstituted phenyl.

The aromatic moiety can alternatively be a substituted or unsubstituted heteroaryl such as, for example, indole, thiophene, imidazole, oxazole, thiazole, pyrazole, pyridine, pyrimidine, quinoline, isoquinoline, quinazoline, quinoxaline, and purine.

When substituted, the phenyl, naphthalenyl or any other aromatic moiety includes one or more substituents such as, but not limited to, alkyl, trihaloalkyl, alkenyl, alkynyl, cycloalkyl, aryl, heteroaryl, heteroalicyclic, halo, nitro, azo, hydroxy, alkoxy, thiohydroxy, thioalkoxy, cyano, and amine.

Exemplary substituted phenyls may be, for example, pentafluoro phenyl, iodophenyl, biphenyl and nitrophenyl.

In some embodiments, at least a portion of, or each peptide in, the aromatic dipeptides comprise two aromatic amino acid residues as described herein.

In some embodiments, at least a portion of, or each peptide in, the plurality of peptides is a homodipeptide (an aromatic homodipeptide), having two aromatic amino acid residues which are identical with respect to their side-chains residue, or in which the two aromatic amino acid residues are identical (the same).

Exemplary aromatic homodipeptides include, but are not limited to, phenylalanine-phenylalanine dipeptide, naphthylalanine-naphthylalanine dipeptide, (pentafluro-phenylalanine)-(pentafluro-phenylalanine) dipeptide, (iodo-phenylalanine)-(iodo-phenylalanine) dipeptide, (4-phenyl phenylalanine)-(4-phenyl phenylalanine) dipeptide and (p-nitro-phenylalanine)-(p-nitro-phenylalanine) dipeptide.

According to some of any of the embodiments described herein, each of the homodipeptides is a phenylalanine-phenylalanine dipeptide.

Herein, "at least a portion" means at least 10%, at least 20%, at least 30%, at least 40%, at least 50%, at least 60%, at least 70%, at least 80%, at least 90%, at least 95%, at least 98%, or at least 99%.

According to the present embodiments, the plurality of aromatic dipeptides forming the nanostructure comprises two or more types of peptides.

In some embodiments, at least one type of the aromatic dipeptides is an aromatic homodipeptide.

In some embodiments, each of the aromatic dipeptides is an aromatic homodipeptide.

The aromatic dipeptides of the two or more types can be the same as or different.

In some embodiments, all of the aromatic dipeptides in the plurality of peptides forming the nanostructure are the same, that is all have the same amino acid residues, and the same type of peptide bond linking therebetween.

In some of any of the embodiments of the present invention, the two or more types of aromatic dipeptides differ from one another by the net charge thereof.

The phrase "net charge" refers to the total charge of the peptide when ionized in an aqueous solution at pH 7.

According to some embodiments of the present invention, the two types of aromatic dipeptides differ from one another by the presence/absence of an end-capping moiety, which masks the charge of one terminus of the peptide.

In some of any of the embodiments of the present invention, at least one type of the aromatic dipeptides is an end-capping modified aromatic dipeptide and at least another type of the aromatic dipeptides is a non-modified aromatic dipeptide.

By "non-modified aromatic dipeptide" it is meant an aromatic dipeptide as described herein in any of the respective embodiments, featuring a free amine group at its N-terminus and a free carboxylic group at its C-terminus. A non-modified peptide is typically zwitterionic and features a neutral net charge.

The phrase "end-capping modified peptide", as used herein, refers to a peptide which has been modified at the N-(amine) terminus and/or the C-(carboxyl) terminus thereof. The end-capping modification refers to the attachment of a chemical moiety to the terminus, so as to form a cap. Such a chemical moiety is referred to herein as an end capping moiety and is typically also referred to herein and in the art, interchangeably, as a peptide protecting moiety or group.

End-capping modified peptides which have been modified at the N-terminus are also referred to herein and in the art as "N-terminus modified peptides" or "N-capped peptides".

End-capping modified peptides which have been modified at the C-terminus are also referred to herein and in the art as "C-terminus modified peptides" or "C-capped peptides".

The phrase "end-capping moiety", as used herein, refers to a moiety that when attached to the terminus of the peptide, modifies the end-capping or terminus/termini of the peptide (namely, modifies the amine and/or carboxylic groups at the peptide's terminus). The end-capping modification typically results in masking the charge of the peptide terminus, and/or altering chemical features thereof, such as, hydrophobicity, hydrophillicity, reactivity, solubility and the like. Examples of moieties suitable for peptide end-capping modification can be found, for example, in Green et al., "Protective Groups in Organic Chemistry", (Wiley, 2.sup.nd ed. 1991) and Harrison et al., "Compendium of Synthetic Organic Methods", Vols. 1-8 (John Wiley and Sons, 1971-1996).

Representative examples of N-terminus end-capping moieties include, but are not limited to, formyl, acetyl (also denoted herein as "Ac"), trifluoroacetyl, benzyl, benzyloxycarbonyl (also denoted herein as "Cbz"), tert-butoxycarbonyl (also denote d herein as "Boc"), trimethylsilyl (also denoted "TMS"), 2-trimethylsilyl-ethanesulfonyl (also denoted "SES"), trityl and substituted trityl groups, allyloxycarbonyl, 9-fluorenylmethyloxycarbonyl (also denoted herein as "Fmoc"), and nitro-veratryloxycarbonyl ("NVOC").

Representative examples of C-terminus end-capping moieties are typically moieties that lead to acylation of the carboxy group at the C-terminus and include, but are not limited to, benzyl and trityl ethers as well as alkyl ethers, tetrahydropyranyl ethers, trialkylsilyl ethers, allyl ethers, monomethoxytrityl and dimethoxytrityl.

Alternatively the —COOH group of the C-terminus end-capping may be modified to an amide group.

Other end-capping modifications of peptides include replacement of the amine and/or carboxyl terminal groups by a different moiety, such as hydroxyl, thiol, halide, alkyl, aryl, alkoxy, aryloxy and the like, as these terms are defined hereinbelow.

In some embodiment of the present invention, the end-capping modified peptides are modified only at the N-terminus or the C-terminus thereof, resulting in a nanostructure that has a negative net charge or a positive net charge, respectively.

The N-terminus or C-terminus end-capping moiety can be aromatic or non-aromatic.

According to some embodiments of the present invention, the end-capping modified peptide is modified by one or more non-aromatic end capping moiety(ies). Representative examples of non-aromatic end capping moieties suitable for N-terminus modification include, without limitation, formyl, acetyl trifluoroacetyl, tert-butoxycarbonyl (t-BOC), trimethylsilyl, and 2-trimethylsilyl-ethanesulfonyl. Representative examples of non-aromatic end capping moieties suitable for C-terminus modification include, without limitation, amides, allyloxycarbonyl, trialkylsilyl ethers and allyl ethers.

According to some embodiments of the present invention, the end-capping modified peptide is modified by a non-aromatic end capping moiety at its N-terminus.

According to some embodiments of the present invention, the end-capping modified peptide is modified by t-BOC at its N-terminus.

According to a preferred embodiment of the present invention, the end-capping modified aromatic dipeptides are homodipeptides, having two aromatic amino acid residues which are identical with respect to their side-chains residue.

Representative examples of such end-capping modified homodipeptides include, without limitation, an end-capping modified naphthylalanine-naphthylalanine (Nal-Nal) dipeptide, end-capping modified (pentafluro-phenylalanine)-(pentafluro-phenylalanine) dipeptide, end-capping modified (iodo-phenylalanine)-(iodo-phenylalanine) dipeptide, end-capping modified (4-phenyl phenylalanine)-(4-phenyl phenylalanine) and end-capping modified (p-nitro-phenylalanine)-(p-nitro-phenylalanine).

According to some of any of the embodiments described herein, each of the end-capping modified dipeptides comprises a non-aromatic end capping moiety.

According to some of any of the embodiments described herein, each of the end-capping modified dipeptides is an N-terminus modified peptide.

According to some of any of the embodiments described herein, the non-aromatic end capping moiety is tert-butoxycarbonyl (also referred to herein as t-Boc or simply as Boc).

According to some of any of the embodiments described herein, each of the end-capping modified dipeptides is a homodipeptide.

According to some of any of the embodiments described herein, each of the non-modified aromatic dipeptides is a homodipeptide.

According to some of any of the embodiments described herein, each of the end-capping modified dipeptides is a homodipeptide and each of the non-modified aromatic dipeptides is a homodipeptide.

The aromatic homodipeptides can be the same or different.

According to some of any of the embodiments described herein, the aromatic homodipeptides of the end-capping modified dipeptides and the aromatic homodipeptides of the non-modified dipeptides are the same, and the two or more types of the aromatic dipeptides differ from one another by nature of one or more terminus/termini, for example, one type of the aromatic homodipeptides is non-modified, and one or more types of the aromatic homodipeptides is end-capping modified.

According to some of these embodiments, the plurality of aromatic dipeptides comprises, or consists of, a plurality of aromatic homodipeptides which are identical to one another with respect to the aromatic side chains of each peptide, wherein one type of the peptides include non-modified peptides and another type of the peptides include N-terminus modified peptides, as described herein in any of the respective embodiments.

In exemplary, non-limiting, embodiments of the present invention, all the aromatic dipeptides are diphenylalanine peptides (also referred to herein as Phe-Phe or FF). One type of these aromatic dipeptides is non-modified and the other type is N-terminus modified. In some embodiments, the N-terminus modified peptides are Boc-FF.

As demonstrated in the Examples section that follows, and is further discussed herein, the nanostructure formed of the two or more types of aromatic dipeptides as described herein features chemical, morphological and dimensional properties which differ from the respective properties of nanostructures made of only one type of aromatic dipeptides. These properties can be controlled or regulated by manipulating the molar ratio of the two or more types of peptides.

According to some of any of the embodiments described herein, the hybrid nanostructure is generally shaped as a closed tubular structure, that is, one or both ends of the tube is/are capped.

According to some of any of the embodiments described herein, the tubular nanostructure is characterized by a length that is smaller than a length of a tubular structure made of only the non-modified aromatic dipeptide.

According to some of any of the embodiments described herein, the tubular structure is characterized by a length that is smaller by at least 10%, or at least 20%, or at least 30%, or at least 40%, or at least 50%, of a length of a tubular structure made of only the non-modified aromatic dipeptide.

The Composition:

According to an aspect of some embodiments of the present invention there is provided a composition comprising a plurality of tubular nanostructures, at least a portion, or each, of the nanostructures being a hybrid nanostructure as described herein in any of the respective embodiments and any combination thereof (hybrid, preferably tubular, nanostructures in which two or more types of aromatic dipeptides are co-assembled).

A composition as described herein comprises a plurality of hybrid nanostructures as described herein, optionally in solution, and further optionally as mixed with other (e.g., peptide-based) nanostructures.

In some embodiments, a composition as described herein consists of a plurality of hybrid nanostructures as described herein, optionally in solution.

In some embodiments, the composition consists of a plurality of hybrid nanostructures as described herein.

According to some of any of the embodiments described herein, at least 50%, or at least 60%, or at least 70%, or at least 80% or at least 90%, or substantially all, of the nanostructures are characterized as closed tubular structures, as described herein.

According to some of any of the embodiments described herein, an average length and/or length distribution of the plurality of tubular nanostructures of the present embodiments in the composition is determined by a molar ratio of the two types of aromatic dipeptides.

According to some of any of the embodiments described herein, the molar ratio of the end-capping modified aromatic homodipeptide and the non-modified aromatic homodipeptide ranges from 1:1 to 1:100 or from 1:2 to 1:100, or from 1:3 to 1:100, or from 1:4 to 1:100, or from 1:5 to 1:100, including any subranges and intermediate values therebetween. According to some of any of the embodiments described herein, the molar ratio ranges from 1:4 to 1:50, or from 1:4 to 1:40, or from 1:4 to 1:30, or from 1:4 to 1:20, including any subranges and intermediate values therebetween.

According to some of any of the embodiments described herein, the molar ratio ranges from 1:9 to 1:40, or from 1:9 to 1:20, including any subranges and intermediate values therebetween.

Generally, but not obligatory, the average length of the nanostructures decreases as the relative concentration of the end-capping modified peptide is increased, that is, as the molar ratio of the end-capping modified peptide to non-modified peptide increases. For example, an average length of nanostructures formed at a molar ratio of 1:4 is shorter than an average length of nanostructures formed at a molar ratio of 1:50. It is to be noted that as used herein, a molar ratio of 1:4 is considered higher than a molar ratio of 1:50.

According to some embodiments of the present invention, at least 80% of the nanostructures are characterized by a length smaller than 10 microns.

According to some embodiments of the present invention, a molar ratio of the two or more different types of aromatic dipeptides in the plurality of aromatic dipeptides is such that provides tubular nanostructures characterized by a length as described herein.

According to an aspect of some embodiments of the present invention the composition comprises a plurality of tubular nanostructures, wherein at least 80% of said nanostructures are characterized by a length smaller than 10 microns, wherein a molar ratio of said at least two types of aromatic dipeptides in said plurality of aromatic dipeptides is such that provides tubular nanostructures characterized by said length.

Determining the molar ratio at which an indicated length, at an indicated occupational fraction, of a plurality of nanostructures can be achieved, is within the common knowledge of any person skilled in the art. In some embodiments, this can be done in accordance with the experimental procedure described in the Examples section that follows. Any other methodology for determining a length distribution is contemplated. Data provided for a few molar ratio can be extrapolated for determining length distribution for other molar ratios. Alternatively, this can be done using theoretical calculations, based, for example, on Cohen et al. *J. Chem. Phys.* 2011, 135, 065107; and Michaels et al. *J. Chem. Phys.* 2015, 143, 164901, which are incorporated by reference as if fully set forth herein.

According to some of any of the embodiments described herein, at least 80% of the nanostructures are characterized by a length smaller than 6 microns.

According to some of any of the embodiments described herein, at least 40% of the nanostructures are characterized by a length that ranges from 1 micron to 5 microns.

Figure 5A:
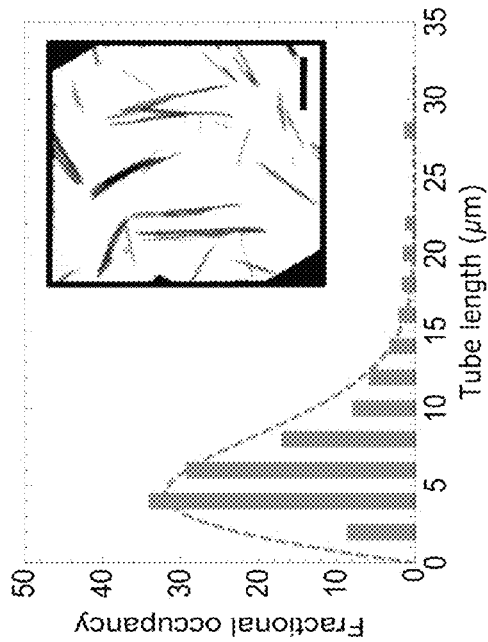
Figure 5B:
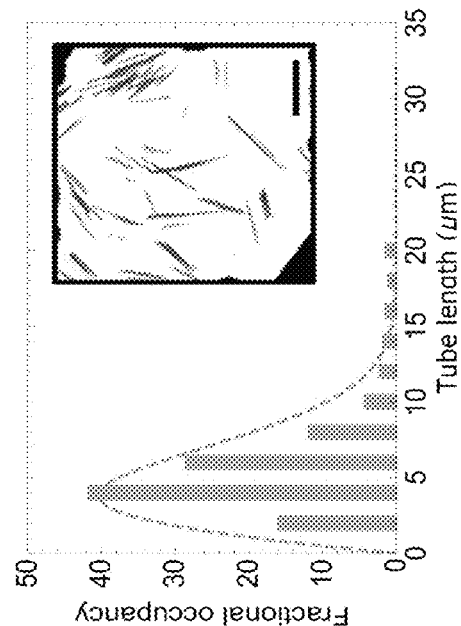
Figure 5C:
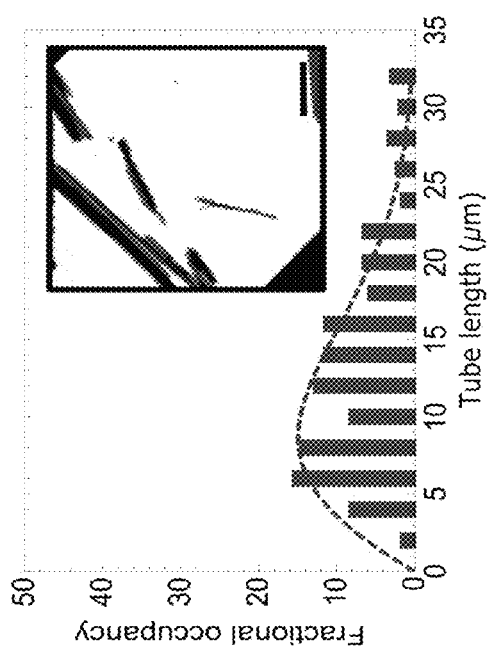
Figure 5D:
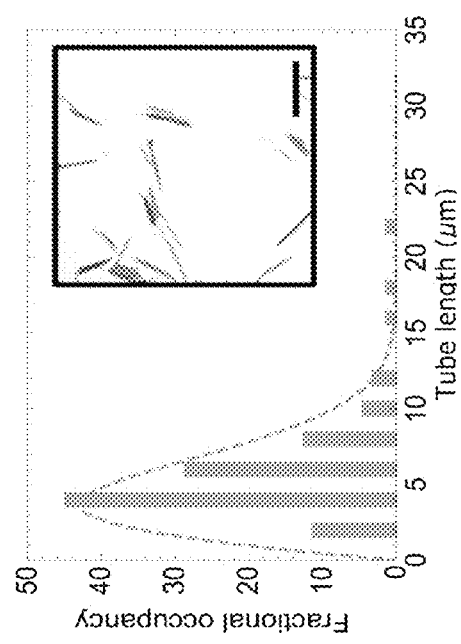

According to some exemplary embodiments, the nanostructures are formed of FF and Boc-FF, and the length and length distribution of the nanostructures at different ratios of the peptides is in accordance with the data presented in FIGS. 5B-D.

According to some embodiments, a composition as described herein is such that an average length of the nanostructures of the present embodiments is smaller by at least 5 microns, or by at least 10 microns, than an average length of a plurality of nanostructures formed of the non-modified aromatic dipeptide.

By "average length" it is meant a length which 50% of the particles do not exceed and 50% of the particles exceed.

The average length can be extracted mathematically from the length distribution of the plurality of tubular nanostructures, by means known in the art.

The length distribution of the plurality of the tubular nanostructures can be measured experimentally by methods known in the art. In some embodiments, the length distribution is extracted from SEM or TEM measurements, as described in the Examples section that follows.

According to an aspect of some embodiments of the present invention there is provided a composition as described herein, characterized by a narrow length distribution.

In some of these embodiments, a length distribution of the tubular nanostructures of the present embodiments has a full-width-at-half-maximum (FWHM) of less than 10 microns.

Herein and in the art, the phrase "length distribution" describes a typically Gaussian distribution of values representing the various lengths of particles (herein the tubular nanostructures of the present embodiments) and the relative fraction thereof in the particle's population (fractional occupancy).

The phrase "a full-width-at-half-maximum", abbreviated as FWHM, as used herein, refers to the width of a length distribution curve at half the maximum height of the curve. That is, half the maximal value of the curve.

Length distribution curves can be generated experimentally or theoretically, for example, in accordance with the experimental procedure described in the Examples section that follows or any other methodology for determining a length distribution is contemplated.

As the length distribution is narrower, the FWHM value is lower.

In some of these embodiments, at least 50%, or at least 60%, or at least 70%, or at least 80% of the nanostructures feature lengths that differ from one another by no more than 10 microns. That is, the variation in the various lengths of the nanostructure within a major portion of nanostructures does not exceed 10 microns.

In some embodiments, a length of at least 50%, or at least 60%, or at least 70% or at least 80% of the nanostructures of the present embodiments in the composition is within 40% of a length of a longest nanostructure in the composition. That is, a major portion, as indicated, of the plurality of nanostructures in the composition are characterized by a length that is smaller from the longest nanostructure by no more than 60%. In some embodiments, a major portion, as indicated, of the plurality of nanostructures in the composition are characterized by a length that is smaller from the longest nanostructure by no more than 50%, or no more than 40%.

In some embodiments, a length distribution of the plurality tubular nanostructures of the present embodiments in the composition has a full-width-at-half-maximum (FWHM) which is at most 40% of a length of a longest nanostructure in the composition.

According to an aspect of some embodiments of the present invention there is provided a composition as described herein, wherein a length distribution of the tubular nanostructures of the present embodiments has a full-width-at-half-maximum (FWHM) which lower by at least 5 microns, or at least 10 microns, from a full-width-at-half-maximum (FWHM) of a length distribution of nanostructures formed of said non-modified aromatic dipeptide.

In some of any of the embodiments defining the length distribution of the plurality of nanostructures in the composition, at least 80% of the nanostructures are characterized by a length smaller than 10 microns.

In some of any of the embodiments described herein, a molar ratio of the two (or more) types of aromatic dipeptides in the plurality of aromatic dipeptides is such that provides tubular nanostructures characterized by a length distribution as described herein.

Generally, the length distribution is narrower as the relative concentration of the end-capping modified aromatic dipeptides increases and the molar ratio decreases.

According to some of any of the embodiments described herein, an average length and length distribution, as defined herein, are regulated by determining a molar ratio of the two (or more) aromatic dipeptides forming the plurality of nanostructures in solution.

According to some of any of the embodiments described herein, there is provided a process of controlling (regulating) an average length and/or a length distribution of a composition comprising a plurality of tubular nanostructures, as described herein, formed of a plurality of aromatic dipeptides in solution.

According to some embodiments, this process effected by preparing a plurality of nanostructures in solution, as described herein, wherein the average length and/or length distribution is/are determined by a molar ratio of the end-capping modified aromatic dipeptide and the non-modified aromatic dipeptide.

According to some of any of the embodiments described herein, there is provided a process of preparing a composition comprising a plurality of tubular nanostructures, as described herein, formed of a plurality of aromatic dipeptides in solution, characterized by a pre-determined average length and/or a length distribution.

According to some embodiments, this process is effected by preparing a plurality of nanostructures in solution, as described herein, and selecting a molar ratio of the end-capping modified aromatic dipeptide and the non-modified aromatic dipeptide that provides a selected, desirable or pre-determined average length and/or length distribution of the nanostructures.

The Process:

According to an aspect of some embodiments of the present invention there is provided a process of generating the nanostructure as described herein, the process comprising contacting a first solution comprising a plurality of the end-capping modified aromatic dipeptides, as described herein in any of the respective embodiments, and a first solvent, and at least a second solution comprising a plurality of the non-modified aromatic dipeptides, as described herein in any of the respective embodiments, and a second solvent, to thereby obtain a mixture of the first and second solutions.

In some embodiments, the contacting is effected at an elevated temperature (e.g., higher than 40° C., or higher than 50, 60 or 70° C.).

In some embodiments, one of the solutions is heated to an elevated temperature and the other solution is added to the heated solution.

In some embodiments, upon the contacting, the obtained mixture is allowed to cool down. In some embodiments, the nanostructures are formed during or upon said cooling.

In some embodiments, a time period during which the plurality of nanostructures is formed ranges from a few minutes to a few hours, for example, from 10 minutes to 10 hours.

In some embodiments, at least 20% of the peptides self-assemble to form the plurality of nanostructures.

In some embodiments, at least one of the first and second solvents is an aqueous solution (e.g., water).

In some embodiments, the first solvent is water and the second solvent is a water-miscible organic solvent. Non-limiting examples of water-miscible solvents include alcohols, for example, ethanol, propanol, isopropyl alcohol and the like. Any other water-miscible solvents are contemplated.

In some embodiments, the second solvent is selected such that the end-capping modified peptide is soluble therein.

In some embodiments, the second solvent is ethanol.

Applications:

Generally, the hybrid nanostructures of the present embodiments can be used in various applications which involve the use of nanoscopic elements.

Such applications are known in the art and disclosed in U.S. Pat. Nos. 5,581,091, 6,383,923, 6,426,134, 6,428,811, 6,428,811, 6,504,292, 6,530,944, 6,559,468, 6,579,742, 6,586,095, 6,628,053 and in U.S. Patent Application Nos. 20020053257, 20020054461, 20020175618, 20020180077, 20020187504, 20030089899, 20030096113, 20030121764, 20030141189, 20030165074, 20030180491-50030197120, all of which are incorporated herein by reference as if fully set forth herein.

According to an aspect of some embodiments of the present invention there is provided an article-of-manufacturing comprising the composition as described herein.

In some embodiments, the article-of-manufacturing comprises a material or matrix in which the plurality of hybrid nanostructures is dispersed.

In some embodiments, the article-of-manufacturing comprises a substrate and the hybrid nanostructures as described herein coating the surface or a portion of the surface of the substrate. Vertical or horizontal alignment of the short hybrid nanostructure can be favorable due to the homogeneous sizes (narrow length distribution) of the nanostructures. In some embodiments, the article-of-manufacturing comprises a material reinforced by the composition as described herein.

According to an aspect of some embodiments of the present invention there is provided a method of reinforcing a material, the method comprising introducing to the material the composition as described herein.

The material to be reinforced according to some embodiments of the present invention can be, for example, a polymer.

Thus, according to yet an additional aspect of the present invention there is provided a polymeric composition, in which a polymer is combined with the hybrid nanostructures of the present embodiments. Preferably, the nanostructure is chemically bonded to, or integrated within the polymer chains, via one or more chemical bond types.

Several attachment configurations can be utilized in order to reinforce polymer chains.

For example, the nanostructures can be linked to one or more chain-terminating group of the polymer chain or to residues of internal polymer groups. The polymer component of the polymeric composition of the present embodiments preferably comprises polymers, including copolymers, which are capable of chemically bonding with the peptides of the nanostructures, or those polymers that can be prepared from one or more monomer precursors capable of bonding with the peptides of the nanostructure either prior to or during polymerization. Representative examples of polymers which may be used include without limitation polyethylene glycol (PEG), polysaccharides, DNA, RNA, poly amino-acids, peptide nucleic acid (PNA).

The polymeric composition described above, can be used for manufacturing many forms of articles, such as filaments, carpets, ropes and the like.

A fiber can be formed from the polymer-nanostructure composition by cutting the polymeric composition into chips and drying. These chips can then be heated under pressure to bond the chips into a plug. This plug can then be heated to a molten state, passed through a mesh screen, and forced through an extrusion orifice. The filament formed by the molten composite material can then be pulled away from the orifice and wound onto a bobbin. Such fibers can be incorporated into bulked continuous filament, and made into carpets, ropes and the like.

Alternatively, the polymeric composition described above can be used as an injection moldable resin for engineering polymers for use in many applications, such as, but not limited to, filters, solenoids and the like.

The nanostructure of the present invention can also be dispersed throughout a matrix material to thereby form a free-form structure. Constructing and arranging composite nodal elements to define a structure circumvents the common practice in the industry of post-fabrication processing operations. Initially, a structure is often fabricated in a mold or by machining and then subjected to post-fabrication processing operations. Post-fabrication processing operations refer to added steps required beyond initial fabrication so that the structure exhibits desired dimensions and tolerance. Typically, post-processing operations include for example, among others, machining, cleaning, polishing, grinding, deburring and hole drilling so as to achieve desired dimensions and tolerance of a fabricated structure.

Exemplary polymeric materials are polymeric formulations used in 3D inkjet printing.

Other polymers and/or articles made therefrom for which integration of the hybrid nanostructures described herein are contemplated.

When another material (e.g., a polymer or a ceramic material) is reinforced with the nanostructure of the present invention, the resulting composition is characterized by a mechanical strength of one or more order of magnitude above the strength of the host material. Such a strong composite material is well suited for many applications such as, but not limited to, in the defense, aerospace and automobile industries.

In some embodiments, the hybrid nanostructures are used for the purpose of delivering energy from one location to the other.

For example, in many industries, there is a great need for more efficient heat transfer fluids. Heat transfer fluids used in today's conventional thermal systems have inherently poor heat transfer properties. Often, millimeter- or micrometer-sized particles are suspended in heat transfer fluids so as to increase the capability of the fluid to deliver heat. Since heat transfer occurs on the surface of a fluid, the nanostructures of the present embodiments can be used for significantly enhancing heat conduction properties of cooling fluids.

Thus, according to some embodiments, there is provided a nanofluid, comprising the nanostructures of the present embodiments suspended in a fluid.

Further provided is a heat transfer device which exploits the above mentioned thermal properties of the nanofluid.

Other applications of the nanostructures of the present embodiments include use thereof in biomedical sciences and in biotechnology such as their use as vehicles for enzyme encapsulation [Chang (2001) Mol. Biotechnol. 17:249-260], DNA transfection [Kneuer (2000) Bioconj. Chem. 11:926-932; Rader (1997) Science 810-814; Koltover (1998) Science 281:78-81], scaffolds for tissue building, biosensors [Cao (2002) Science 297:1536-1540; Demers (2002) Science 296:1836-1838; Park (2002) Science 295:1503-1506] and drug delivery [Ulrich (1999) Chem. Rev. 99:3181-3198;

Lee (2002) Biomacromolecules 3:1115-1119; Murthy (2002) J. Am. Chem. Soc. 124:12398-12399]. For example, drugs can be incorporated onto the nanostructures, for example, by binding through cleavable bonds, or by physical absorption. Alternatively, the nanostructures of the present invention can be coated with viral peptide sequences which promote membrane-permeation. Finally, surface functionalized nanostructures of the present invention can also be used to deliver genetic material into living cells (i.e., transfection).

The relatively short hybrid nanostructures may serve as improved carrier for drug delivery applications.

The nanostructures can be coated by any suitable material, e.g., a conductive material (as in the case of the nanoshells), a semiconductive material or a dielectric material, and can be bounded to other molecules to achieve desired electrical, mechanical, chemical or biological properties. For example, the nanostructures of the present invention can be coated by silver, gold and other conductive materials.

The hybrid nanostructures can further be used in thermoelectric devices.

The nanostructure of the present embodiments can be used to construct a matrix of an artificial tissue, which can be used for surgical training and/or for implantation in a subject during a medical operation. A matrix made of the nanostructures of the present embodiments is likely to be biocompatible and immuno-acceptable by the host, and allow cell which are incorporated into the matrix to grow and assimilate in the surrounding tissue. Furthermore, the matrix, being composed of peptide nanostructures, is biodegradable therefore can be eliminated by natural processes within the host.

For a cell implant or other type of viable cell insert to be effective, the cells must undergo any reorganization, growth and differentiation which is required to permit the cells to achieve normal functioning in the body. For a three-dimensional matrix holding the cells in a unitary mass to promote this result, it should satisfy all of the following criteria. The process used for forming the matrix must be rapid and sufficiently gentle to prevent cellular damage. The materials used must permit a rapid reaction under these gentle conditions. The process should allow shape and size control. For a process to be generally applicable for a variety of cells, it should produce shapes having controllable final cell densities ranging from particles containing one to a few cells to shapes containing cells at a density approaching the cell density in tissue, i.e., approximately from $10^9$-$10^{10}$ cells per cubic centimeter.

The ranges of size of the nanostructures should be exploited to promote cell viability in a physiological environment. Soon after implantation, diffusion of oxygen and nutrients into the central interior of particles having excessive diameters would be insufficient, causing death of cells in the central interior.

The final nanostructure-made matrix must be nontoxic and biocompatible, and it can be biodegradable. The process should provide the ability to vary and control the matrix porosity to the level necessary to permit the requisite diffusion of nutrients and macromolecules. The process should be able to provide matrices which partially immobilize the cells to encourage cell-to-cell contact while being sufficiently loose to permit cell movement which may be necessary for rearrangement during tissue development. The matrix composition should also be susceptible to the degradation, removal or alteration in the host environment which is required for entry of the host cells into the matrix during the vascularization process.

All the above mentioned criteria can be satisfied with a matrix consisting of the nanostructures of the present embodiments.

The hybrid nanostructured can be used in the field of micro- and sub-microelectronic circuitry and devices.

The nanostructures can be deposited onto a surface of a substrate, or a portion thereof, in the manufacturing of miniaturized electrical circuitry and templates thereof, area and spatial detectors, sensors, biosensors and templates thereof, fabrication of nano-patterned bio-structures and templates thereof, fabrication of nano-patterned bio-structures and templates for gases adhesion (air purification), fabrication of bio-structures and templates for contaminants selective adhesion (water and other liquids purification), fabrication of transmissive coats, such as hydrophobic or superhydrophobic coats for self-cleaning surfaces (e.g., the so called "smart window") and solar cells, fabrication of coats with controllable properties (transparency, reflectivity and/or absorption) for various electromagnetic radiation ranges (X-ray, UV, visible, IR, RF), fabrication of electrochemical devices including batteries, accumulators, capacitors and other electrical storage devices, fabrication of microfluidic devices, engineering of biological surfaces including tissue engineering and patterned biological cues, fabrication of bio-structures and templates for cell growth confinement, fabrication of bio-structures and templates for specific biomolecules coatings for gas storage, ion exchange, various catalysis, guest adsorption, and the likes.

In some embodiments, the article-of-manufacturing is a medical device which includes the nanostructured deposited on a solid substrate and occupying at least a portion of a surface of the substrate.

According to some embodiments of the present invention, the medical device is designed for implanting the medical device in a bodily organ. As used herein, the term "organ" further encompasses a bodily cavity.

The organ can be, for example, a pulmonary cavity, a heart or heart cavity, a bodily cavity, an organ cavity, a blood vessel, an artery, a vein, a muscle, a bone, a kidney, a capillary, the space between dermal layers, an organ of the female or male reproductive system, an organ of the digestive tract and any other visceral organ.

The medical device according to this embodiment of the present invention typically includes a device structure onto which a nanostructures are deposited on at least parts of its surface. The device structure can be, for example, metallic structure and thus may be comprised of a biocompatible metal or mixture of metals such as gold or platinum. Alternatively, the device structure may be comprised of other biocompatible matrices. These can include, for example, plastics, glass, silicon, polymers, resins, and may include at least one component such as, for example, polyurethane, cellulose ester, polyethylene glycol, polyvinyl acetate, dextran, gelatin, collagen, elastin, laminin, fibronectin, vitronectin, heparin, segmented polyurethane-urea/heparin, poly-L-lactic acid, fibrin, cellulose and amorphous or structured carbon such as in fullerenes, and any combination thereof.

In cases where a biodegradable implantable device is desired, the device structure can be comprised of a biocompatible matrix that is biodegradable. Biodegradable matrices can include, for example, biodegradable polymers such as poly-L-lactic acid.

Optionally, the device structure may be comprised of biocompatible metal(s) coated with other biocompatible matrix.

The substrate coated with nanostructures can be additionally used to form a part of an electrical energy storage device, such as, but not limited to, electrical cell, electrochemical cell or power source.

Two types of electrical energy storage devices are contemplated by the present embodiments. In some embodiments, the electrical energy storage device is embodied as a battery device whereby charge storage is achieved via electron transfer that produces a redox reaction. In some embodiments, the electrical energy storage device is embodied as an electric double-layer capacitor, also known as a supercapacitor, whereby the storage of electrical energy is electrostatic, substantially devoid of any electron transfer.

To avoid possible confusion between a single cell and electrical energy storage device which may have one or more cells, the terms "cell" and electrical energy storage device are used interchangeably, except where the context clearly indicates otherwise. As used herein the term "electrode" is used to mean a phase through which charge is carried by electronic movement. Electrodes can be metals or semiconductors, and they can be solid or liquid. Also as used herein, the term "electrolyte" is generally defined as a phase through which charge is carried by the movement of ions. Electrolytes may be any phase on the continuum of liquid to solid, including gels, pastes, fused salts, or ionically conducting solids.

Additionally, a substrate coated with the hybrid nanostructures can be used to form a part of a sensor device, for example, an electrochemical sensor. In exemplary embodiments, the nanostructures are deposited in at least a portion of a surface of an electrode in the device.

In some embodiments, the device is a microfluidic device and the nanostructures are deposited on at least a portion of the microfluidic device.

Applications for the microfluidic device of these embodiments include, without limitation, genetic, chemical, biochemical, pharmaceutical, biomedical, chromatography, integrated circuit cooling, ink-jet printing, medical, radiological and environmental applications. The medical applications include without limitation, diagnostic and patient management such as implanted drug dispensing systems. The environmental applications include, without limitation, detecting hazardous materials or conditions such as air or water pollutants, chemical agents, biological organisms or radiological conditions. The genetic and biochemical applications include, without limitation, testing and/or analysis of DNA, and other macro or smaller molecules, or reactions between such molecules in a microfluidic device in an approach known as "lab-on-chip".

The microfluidic device of the present embodiments can also be used in chemical and biochemical sensing, molecular separations, drug delivery and other forefront technologies. In a manner similar to that for microelectronics, the microfluidic device of the present embodiments enables the fabrication of highly integrated devices applicable to high throughput, low volume, automatable chemical and biochemical analyses and syntheses. Fluids which can be used in the microfluidic device of the present embodiments include water, whole blood samples, bacterial cell suspensions, protein or antibody or nucleic acid solutions and various buffers.

The microfluidic device of the present embodiments can be used to obtain a variety of measurements including, without limitation, molecular diffusion coefficients, fluid viscosity, pH, chemical binding coefficients and enzyme reaction kinetics. Also contemplated are other applications, including, without limitation, capillary electrophoresis, isoelectric focusing, immunoassays, flow cytometry, sample injection of proteins for analysis via mass spectrometry, sample injection of air or water samples for analysis via flamespectrometry, polymerase chain reaction (PCR) amplification, DNA analysis, cell manipulation, cell separation, cell patterning and chemical gradient formation.

For self-cleaning surfaces, the hybrid nanostructures can be applied to coat the entire surface, substantially uniformly. To enhance the hydrophobic property of the deposition, the nanostructures can be arranged generally perpendicularly to the substrate.

In some embodiments, the substrate and/or the nanostructures can be transmissive, reflective or adsorptive to any type of electromagnetic radiation, and can be used in an optical device. In some embodiments the nanostructures can coat a window glass, solar cell panels, glassware, lenses and the like to form a self-cleaning transparent object.

In some embodiments, the nanostructures can coat black mirrors used in solar cell devices.

In some embodiments, the nanostructures can be used in antibacterial and antifouling applications, by being deposited on substrates in which such applications are desirable.

Any other article-of-manufacturing and applications in which dispersing peptide nanostructures in a matrix or depositing nanostructures on a substrate's surface, are beneficial, are contemplated.

Exemplary such articles and applications are described, for example, in WO 2009/034566, and WO 2006/027780, which are incorporated by reference as if fully set for herein.

The end-capping modification of the peptides forming the nanostructures described herein can be further utilized for incorporating into the nanostructure a labeling moiety. Nanostructures composed of such labeled peptides can be utilized in a variety of applications, including, for example, tracing and tracking location of nanoelements composed of the nanostructures of the present invention in mechanical devices and electronic circuitry; and tracing, tracking and diagnosing concentrations of the nanostructures of the present invention in a living tissue, cell or host.

Thus, according to an embodiment of the present invention, the one or more end-capping modified peptide comprises a labeling moiety. The labeling moiety can form a part of the end-capping moiety or can be the end-capping moiety itself.

As used herein, the phrase "labeling moiety" describes a detectable moiety or a probe which can be identified and traced by a detector using known techniques such as IR, NMR, X-ray diffraction and imaging, HPLC, PET, SPECT, MRI, CT and the like.

Representative examples of labeling moieties include, without limitation, fluorescent moieties, chromophores, phosphorescent moieties, radioactive labeling moieties, heavy metal clusters, as well as any other known detectable moieties.

As used herein, the term "chromophore" refers to a chemical moiety that, when attached to an end-capping moiety or is an end-capping moiety, renders the latter colored and thus visible when various spectrophotometric measurements are applied.

The phrase "fluorescent moiety" refers to a chemical moiety that emits light at a specific wavelength during exposure to radiation from an external source.

The phrase "phosphorescent moiety" refers to a chemical moiety emitting light without appreciable heat or external excitation as by slow oxidation of phosphorous.

A heavy metal cluster can be for example a cluster of gold atoms used, for example, for labeling in electron microscopy or X-ray imaging techniques.

Radiolabeled compounds can be almost any chemical moiety into which a radioactive isotope is incorporated. A radioactive isotope is an element which emits radiation and includes, for example, an α-radiation emitters, a β-radiation emitters or a γ-radiation emitters.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "alkyl" refers to a saturated aliphatic hydrocarbon including straight chain and branched chain groups. Preferably, the alkyl group has 1 to 20 carbon atoms. The alkyl group may be substituted or unsubstituted. When substituted, the substituent group can be, for example, trihaloalkyl, alkenyl, alkynyl, cycloalkyl, aryl, heteroaryl, heteroalicyclic, halo, nitro, azo, hydroxy, alkoxy, thiohydroxy, thioalkoxy, cyano, and amine.

A "cycloalkyl" group refers to an all-carbon monocyclic or fused ring (i.e., rings which share an adjacent pair of carbon atoms) group wherein one of more of the rings does not have a completely conjugated pi-electron system. Examples, without limitation, of cycloalkyl groups are cyclopropane, cyclobutane, cyclopentane, cyclopentene, cyclohexane, cyclohexadiene, cycloheptane, cycloheptatriene, and adamantane. A cycloalkyl group may be substituted or unsubstituted. When substituted, the substituent group can be, for example, alkyl, trihaloalkyl, alkenyl, alkynyl, cycloalkyl, aryl, heteroaryl, heteroalicyclic, halo, nitro, azo, hydroxy, alkoxy, thiohydroxy, thioalkoxy, cyano, and amine.

An "alkenyl" group refers to an alkyl group which consists of at least two carbon atoms and at least one carbon-carbon double bond.

An "alkynyl" group refers to an alkyl group which consists of at least two carbon atoms and at least one carbon-carbon triple bond.

An "aryl" group refers to an all-carbon monocyclic or fused-ring polycyclic (i.e., rings which share adjacent pairs of carbon atoms) groups having a completely conjugated pi-electron system. Examples, without limitation, of aryl groups are phenyl, naphthalenyl and anthracenyl. The aryl group may be substituted or unsubstituted. When substituted, the substituent group can be, for example, alkyl, trihaloalkyl, alkenyl, alkynyl, cycloalkyl, aryl, heteroaryl, heteroalicyclic, halo, nitro, azo, hydroxy, alkoxy, thiohydroxy, thioalkoxy, cyano, and amine.

A "heteroaryl" group refers to a monocyclic or fused ring (i.e., rings which share an adjacent pair of atoms) group having in the ring(s) one or more atoms, such as, for example, nitrogen, oxygen and sulfur and, in addition, having a completely conjugated pi-electron system. Examples, without limitation, of heteroaryl groups include pyrrole, furane, thiophene, imidazole, oxazole, thiazole, pyrazole, pyridine, pyrimidine, quinoline, isoquinoline and purine. The heteroaryl group may be substituted or unsubstituted. When substituted, the substituent group can be, for example, alkyl, trihaloalkyl, alkenyl, alkynyl, cycloalkyl, aryl, heteroaryl, heteroalicyclic, halo, nitro, azo, hydroxy, alkoxy, thiohydroxy, thioalkoxy, cyano, and amine.

A "heteroalicyclic" group refers to a monocyclic or fused ring group having in the ring(s) one or more atoms such as nitrogen, oxygen and sulfur. The rings may also have one or more double bonds. However, the rings do not have a completely conjugated pi-electron system. The heteroalicyclic may be substituted or unsubstituted. When substituted, the substituted group can be, for example, lone pair electrons, alkyl, trihaloalkyl, alkenyl, alkynyl, cycloalkyl, aryl, heteroaryl, heteroalicyclic, halo, nitro, azo, hydroxy, alkoxy, thiohydroxy, thioalkoxy, cyano, and amine. Representative examples are piperidine, piperazine, tetrahydrofuran, tetrahydropyrane, morpholino and the like.

A "hydroxy" group refers to an —OH group.

A "thio", "thiol" or "thiohydroxy" group refers to and —SH group.

An "azide" group refers to a —N=N=N group.

An "alkoxy" group refers to both an —O-alkyl and an —O-cycloalkyl group, as defined herein.

An "aryloxy" group refers to both an —O-aryl and an —O-heteroaryl group, as defined herein.

A "thiohydroxy" group refers to and —SH group.

A "thioalkoxy" group refers to both an —S-alkyl group, and an —S-cycloalkyl group, as defined herein.

A "thioaryloxy" group refers to both an —S-aryl and an —S-heteroaryl group, as defined herein.

A "halo" or "halide" group refers to fluorine, chlorine, bromine or iodine.

A "trihaloalkyl" group refers to an alkyl substituted by three halo groups, as defined herein. A representative example is trihalomethyl.

An "amino" group refers to an —NR'R" group where R' and R" are hydrogen, alkyl, cycloalkyl or aryl.

A "nitro" group refers to an —NO$_2$ group.

A "cyano" group refers to a —C≡N group.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Material and Methods

Materials:

Diphenylalanine (H-Phe-Phe-OH) and Boc-Phe-Phe-OH were purchased from Bachem (Bubendorf, Switzerland);

All other solvents and chemical were purchased from known vendors.

Analyses:

Yield measurements were performed by weighing the end product post-lyophilization. The end product weight was divided by the sum of H-Phe-Phe-OH and Boc-Phe-Phe-OH weights.

Transmission scanning electron microscopy (TEM) measurements were performed by sonicating a 10-μl sample of the peptide solution in a bath sonicator for 5 seconds and thereafter placing the sample on Formvar/carbon mesh 400 copper grids (Electron Microscopy Sciences) for 20 seconds. Samples were then removed using a piece of nitrocellulose paper, and the Cu grids were left to dry at room temperature. Samples were then viewed using a JEOL 1200EX electron microscope operating at 80 kV.

Scanning electron microscopy (SEM) measurements were performed using a JSM JEOL 6300 SEM operating at 5 kV. Samples were put on a glass cover slip, as described hereinbelow, and coated with gold.

High resolution SEM (HR-SEM) measurements were performed using a JSM-6700 field-emission HR-SEM (JEOL, Tokyo, Japan), equipped with a cold field emission gun, operating at 10 kV. Samples were placed on glass slides and were left to dry at room temperature. Samples were then coated with Cr and viewed.

Size distribution of the nanostructure's length were performed by sonicating a 10-μl sample of the peptide solution in a bath sonicator for 5 seconds and thereafter placing the sample on Formvar/carbon mesh 400 copper grids (Electron Microscopy Sciences) for 20 seconds. The sample was then removed using a piece of nitrocellulose paper, and the Cu grids were left to dry at room temperature. Samples were then viewed using a Quanta 200 FEG Environmental Scanning Electron Microscope (ESEM). According to the size bar that was presented by the ESEM for each image many different individual tubes were analyzed for their length. Analysis was done using NIH ImageJ software.

Image analyses and measurements of the peptide nanotube (PNT) size (based on SEM and TEM images) were performed using the free software ImageJ (developed at the NIH). Each TEM and SEM image had a scale bar in μm that was provided by the microscope's software. These scale bars were measured as a straight line, in pixels using the ImageJ tools. The scale bar length in pixels was set as a known distance in μm according to which all the measurable objects in that image were measured. Objects showing their two ends in the frame were measured and listed (an average of 12 images per each FF and BocFF mixture was analyzed). The length distribution, average length and standard deviation of each mixture were calculated from a sampling of 54-958 measured objects.

Light microscopy was performed using a ML8100 light microscope (Meiji Techno).

Assembly kinetic measurements were performed upon preparing solutions of FF only, Boc-FF only and FF:Boc-FF at a 20:1 molar ratio as described hereinbelow. Glass vials containing 15 ml of each solution were left to cool down to room temperature and incubated for 72 hours. In addition, samples of 200 μl were taken from each vial and inserted to a 96-well plate. Absorbance at 400 nm was measured every 15 minutes using a TECAN infinite M200PRO plate reader, for a total time of 17 hours.

Preparation of Nanostructures (General Procedure):

Stock solutions of Boc-Phe-Phe-OH (Boc-FF) dissolved in 100% EtOH (50 mg/ml) and FF dissolved in hot water (DDW) (e.g., 80-90° C.) (2 mg/ml) are prepared.

An amount of the solution of Boc-FF in EtOH is added to an amount of a solution of FF in hot water, ethanol is added, and the obtained mixture is allowed to cool down to room temperature for a time period ranging from about 1 minute to about 6 hours, depending on the preparation volume.

Experimental Results

Preparation of Exemplary Nanostructures:

Using the above-described general procedure, ten different mixtures, of various combinations of Boc-FF and FF solutions, which afford various final concentrations and molar ratios of the peptides, were prepared, as delineated in Table 1 below. The mixtures were allowed to cool down for a time period as indicated hereinabove, and self-assembly in each of the mixtures was monitored by observation (visually determining when the amount of self assembled material ceased to increase).

For SEM measurements, 50 μl samples of each mixture were sonicated in a bath for 2-5 seconds (so as to allow temporary isolation of the obtained self-assembled nanostructures for electron microscopy measurements). Immediately thereafter, a 10 μl drop of the sonicated sample was placed on a glass slide for 20 seconds, and was then removed by touching the edge of the drop with a small piece of filter paper (Whatman), leaving in the slide self-assembled structures that precipitated during the 20 seconds period. The slides were allowed to fully dry and were analyzed thereafter.

Yield was calculated by filtering the material through a 0.45 μm cellulose acetate filter paper, drying the filtrated solution by lyophilization and dividing the end product weight by the weight of the sum of FF and BocFF that were used for the mixture.

At low Boc-FF concentrations, a hybrid spherical/tubular morphology, of closed tubular structures, was observed, with length shorter than the tubular structures of FF alone, yet aggregation is reduced compared to higher Boc-FF concentrations. When Boc-FF was the sole peptide, the

TABLE 1

|  | A | B | C | D | E | F | G | H | I | J |
|---|---|---|---|---|---|---|---|---|---|---|
| FF | 5 ml | 5 ml | 5 ml | 5 ml | 5 ml | 5 ml | 5 ml | 5 ml | 5 ml | — |
| BocFF | — | 400 μl | 200 μl | 100 μl | 50 μl | 25 μl | 12.5 μl | 6.3 μl | 3.1 μl | 216 μl |
| EtOH | 0.4 ml | — | 200 μl | 300 μl | 350 μl | 375 μl | 387.5 μl | 394 μl | 397 μl | 184 μl |
| Water | — | — | — | — | — | — | — | — | — | 5 ml |
| FF Conc. | 6 mM | 6 mM | 6 mM | 6 mM | 6 mM | 6 mM | 6 mM | 6 mM | 6 mM | — |
| BocFF Conc. | — | 9.0 mM | 4.5 mM | 2.3 mM | 1.1 mM | 0.6 mM | 0.3 mM | 0.15 mM | 0.08 mM | 4.8 mM |
| FF:BocFF molar ratio | — | 0.66:1 | 1.33:1 | 2.6:1 | 5:1 | 10:1 | 20:1 | 40:1 | 75:1 | — |

FIG. 1 presents the calculated yield of the obtained hybrid nanostructures.

Morphology:

FIGS. 2A-J present light microscopy images of peptide nanostructures prepared from mixtures A-J depicted in Table 1 above. As shown in these figures, nanostructures made of a mixture of BocFF and FF exhibit properties which are different from those made of one type of dipeptide, whereby these properties vary in accordance with the molar ratio of the dipeptides in the initial mixture. At 6:1, 10:1 and 20:1 FF:BocFF molar ratios (see FIGS. 2E, 2F, 2G, 3E, 3F and 3G), short tubular structures are observed, suggesting an interference of the BocFF dipeptides with the growth of fibrillar nanostructures of FF.

FIGS. 3A-H present SEM images of the nanostructures made of the different mixtures, as follows:

Solely FF (mixture a; FIG. 3A); 9.0 mM BocFF (mixture b; FIG. 3B); 4.5 mM BocFF (mixture c; FIG. 3C); 2.3 mM BocFF (mixture d; FIG. 3D); 1.1 mM BocFF (mixture e; FIG. 3E); 0.6 mM BocFF (mixture f. FIG. 3F); 0.3 mM BocFF (mixture g, FIG. 3G); 0.15 mM BocFF (mixture h; FIG. 3H); 0.08 mM BocFF (mixture i, FIG. 3I); and 4.8 mM BocFF solely (mixture j; FIG. 3J).

As can be seen, ordered elongated tubular structures were formed from a solution of FF upon cooling down to room temperature. Due to the hydrophobic nature of the peptides, nanostructures tend to adhere to one another and form bundles. In order to distinguish between each individual nanostructure, a short sonication was applied on the nanotubes solution prior to the preparation of the sample for electron microscopy imaging. Scanning electron micrographs demonstrate the high aspect ratio of the tubular structure (see, FIG. 3A).

Nanostructures formed from a combination of FF and Boc-FF, with the latter at high concentration, exhibited a hybrid spherical/tubular morphology, generally of closed tubular structures having a short length (e.g., lower than 4 μm). All hybrid nanostructures features a capped architecture which is distinct from the hollow nature of the FF tubes.

Addition of Boc-FF at an FF:Boc-FF molar ratio of 20:1 resulted in the shortening of the ordered structures (see, FIG. 3G). Elevating the ratio of Boc-FF in the solution to 10:1 or 5:1 (FF:Boc-FF) resulted in the additional shortening of the tubes (see, FIGS. 3F and 3E, respectively). A capping architecture is also observed on the structures that are assembled by Boc-FF solely (see, FIG. 3I).

formed nanostructures exhibited also a population of bundles of short and thin tubular structures. When FF was the sole peptide, most of the formed nanostructures were discrete, long and exhibited a tubular morphology.

Kinetics:

The kinetics of the FF peptide self-assembly process into ordered elongated tubular structures was monitored by the turbidity of the structures solution, shown in FIG. 4A. The self-assembly kinetics of the co-polymers in comparison to each of the peptides alone.

The FF peptide is soluble in water at a concentration of 2 mg/ml at 80° C., while gradually cooling off the solution to room temperature results in peptide self-assembly into tubular structures. When cooling the solution to room temperature the transparency is decreased, and after 20 minutes, the solution becomes opaque and gradually more turbid, as shown in FIG. 4A, upper panel. Dissolving the Boc-FF at a concentration of 0.125 mg/ml at 80° C. results in a transparent solution that remains clear even after 72 hours, as shown in FIG. 4A, middle panel.

However, dissolving both the FF peptide at a concentration of 2 mg/ml together with the Boc-FF peptide at a concentration of 0.125 mg/ml at 80° C. shows a different pattern than those of the individual peptide assemblies. As shown in FIG. 4A, lower panel, when cooling the transparent solution of the two peptides (time=0), opacity is increased only after approximately 30 minutes. After 40 minutes, the solution is less opaque than that containing FF only. After 60 minutes, the co-assembly solution is more turbid than the FF solution.

To quantify the kinetics of the self-assembly process, the absorbance of these solutions at a wavelength of 400 nm over time was monitored. As shown in FIG. 4B, the absorbance of the FF solution starts to increase after approximately 350 minutes, and reaches an O.D. of 0.4 while the absorbance of the Boc-FF solution remains around zero. The absorbance of the co-assembly solution remained low up to 800 minutes, then gradually increased until reaching an O.D of 1.3.

These observations demonstrate that the FF and Boc-FF indeed co-assemble to form hybrid tubular structures. Without being bound by any particular theory, it is assumed that the difference between the time frames of the vials turbidity assay and the absorbance measured at 400 nm are due to the different solution volumes available in each experiment, which affect the assembly kinetics.

Length Distribution:

FIGS. 5A-D present the length distribution of nanostructures, extracted from EM measurements as described hereinabove, obtained from mixture A (FF alone; FIG. 5A); mixture G (FF:BocFF 20:1; FIG. 5B); mixture E (FF:BocFF 5:1; FIG. 5C) and mixture F (FF:BocFF' 10:1; FIG. 5D). Insets show the TEM image of each sample.

As shown therein, in FF:BocFF molar ratios ranging from 20:1 to 5:1, a narrower distribution is observed, with most nanostructures featuring a length lower than 10 µm, or even lower than 6 µm.

While the length of the FF nanotubes ranges between 2 µm to 32 µm [N (number of nanotubes measured)=287] (FIG. 5A) and the 95 percentile was 26 µm, the addition of Boc-FF at a molar ratio of 20:1 (FF:Boc-FF) results in shortening of the assemblies. More than 95% of the tubes are 12 µm long or less (N=958) (FIG. 5B). The elevation of the Boc-FF concentrations to FF:Boc-FF ratios of 10:1 (N=312) and 5:1 (N=852) result in 94-96% of the tubes to be 10 µm or less and 8 µm or less, respectively (FIGS. 5C and 5D).

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A composition comprising a plurality of tubular nanostructures, wherein at least 80% of said nanostructures are characterized by a length smaller than 10 microns, each of said nanostructures being formed of a plurality of aromatic dipeptides, said plurality of aromatic dipeptides comprising at least two different types of aromatic dipeptides, at least one type of said aromatic dipeptides being an end-capping modified aromatic dipeptide and at least one type of aromatic dipeptides being a non-modified aromatic dipeptide,
   wherein each of said non-modified aromatic dipeptides is a phenylalanine-phenylalanine dipeptide and each of said end-capping modified dipeptides is an N-terminus modified peptide, said end capping moiety being tert-butoxycarbonyl (Boc),
   wherein a molar ratio of said at least two types of aromatic dipeptides in said plurality of aromatic dipeptides is such that provides tubular nanostructures characterized by said length.

2. The composition of claim 1, wherein at least 50% of said nanostructures are characterized as closed tubular structures.

3. The composition of claim 1, wherein at least 80% of said nanostructures are characterized by a length smaller than 8 microns.

4. The composition of claim 1, wherein said molar ratio of said end-capping modified aromatic homodipeptide and said non-modified aromatic homodipeptide ranges from 1:5 to 1:100.

5. The composition of claim 4, wherein said molar ratio ranges from 1:5 to 1:50.

6. A composition comprising a plurality of tubular nanostructures, each of said nanostructures being formed of a plurality of aromatic dipeptides, said plurality of aromatic dipeptides comprising at least two different types of aromatic dipeptides co-assembled with one another, at least one type of said aromatic dipeptides being an end-capping modified aromatic dipeptide and at least one type of aromatic dipeptides being a non-modified aromatic dipeptide,
   wherein each of said non-modified aromatic dipeptides is a phenylalanine-phenylalanine dipeptide and each of said end-capping modified dipeptides is an N-terminus modified peptide, said end capping moiety being tert-butoxycarbonyl (Boc),
   wherein a length distribution of said nanostructures has a full-width-at-half-maximum (FWHM) of less than 10 microns.

7. The composition of claim 6, wherein at least 50% of said nanostructures are characterized as closed tubular structures.

8. The composition of claim 6, wherein at least 80% of said nanostructures are characterized by a length smaller than 10 microns.

9. The composition of claim 6, wherein a molar ratio of said at least two types of aromatic dipeptides in said plurality of aromatic dipeptides is such that provides tubular nanostructures characterized by said length distribution.

10. The composition of claim 9, wherein said molar ratio of said end-capping modified aromatic homodipeptide and said non-modified aromatic homodipeptide ranges from 1:5 to 1:100.

11. The composition of claim 10, wherein said molar ratio ranges from 1:5 to 1:50.

12. An article-of-manufacturing comprising the composition of claim 1.

13. The article-of-manufacturing of claim 12, comprising a material reinforced by said composition.

14. A method of reinforcing a material, the method comprising introducing to the material the composition of claim 1.

15. An article-of-manufacturing comprising the composition of claim 6.

16. The article-of-manufacturing of claim 15, comprising a material reinforced by said composition.

17. A method of reinforcing a material, the method comprising introducing to the material the composition of claim 6.

* * * * *